(12) United States Patent
Debinski et al.

(10) Patent No.: US 9,975,942 B2
(45) Date of Patent: May 22, 2018

(54) EPHA3 AND MULTI-VALENT TARGETING OF TUMORS

(71) Applicant: Wake Forest University Health Sciences, Winston-Salem, NC (US)

(72) Inventors: Waldemar Debinski, Winston-Salem, NC (US); Carla Lema Tome, Winston-Salem, NC (US); Sara Ferluga, Trieste (IT); Poonam S. Sonawane, Winston-Salem, NC (US)

(73) Assignee: Wake Forest University Health Services, Winston-Salem, NC (US)

( * ) Notice: Subject to any disclaimer, the term of this patent is extended or adjusted under 35 U.S.C. 154(b) by 0 days. days.

(21) Appl. No.: 15/035,560

(22) PCT Filed: Nov. 11, 2014

(86) PCT No.: PCT/US2014/064983
§ 371 (c)(1),
(2) Date: May 10, 2016

(87) PCT Pub. No.: WO2015/070210
PCT Pub. Date: May 14, 2015

(65) Prior Publication Data
US 2016/0297863 A1    Oct. 13, 2016

Related U.S. Application Data

(60) Provisional application No. 62/036,262, filed on Aug. 12, 2014, provisional application No. 61/902,568, filed on Nov. 11, 2013.

(51) Int. Cl.
| | | |
|---|---|---|
| *C07K 14/705* | (2006.01) | |
| *C07K 14/52* | (2006.01) | |
| *C07K 14/54* | (2006.01) | |
| *G01N 33/574* | (2006.01) | |
| *A61K 38/00* | (2006.01) | |

(52) U.S. Cl.
CPC ............ *C07K 14/705* (2013.01); *C07K 14/52* (2013.01); *C07K 14/5437* (2013.01); *G01N 33/57492* (2013.01); *A61K 38/00* (2013.01); *C07K 2319/01* (2013.01); *C07K 2319/06* (2013.01); *C07K 2319/09* (2013.01); *C07K 2319/30* (2013.01); *C07K 2319/33* (2013.01); *C07K 2319/55* (2013.01); *C07K 2319/74* (2013.01)

(58) Field of Classification Search
CPC ... C07K 14/705; C07K 14/5437; C07K 14/52
USPC ..................................................... 424/133.1
See application file for complete search history.

(56) References Cited

U.S. PATENT DOCUMENTS

| | | |
|---|---|---|
| 5,328,984 A | 7/1994 | Pastan et al. |
| 5,614,191 A | 3/1997 | Puri et al. |
| 5,919,456 A | 7/1999 | Puri et al. |
| 6,296,843 B1 | 10/2001 | Debinski |
| 6,428,788 B1 | 8/2002 | Debinski et al. |
| 6,518,061 B1 | 2/2003 | Puri et al. |
| 6,576,232 B1 | 6/2003 | Debinski et al. |
| 6,630,576 B2 | 10/2003 | Debinski |
| 6,884,603 B2 | 4/2005 | Debinski et al. |
| 7,078,030 B2 | 7/2006 | Johnson et al. |
| 7,517,964 B2 | 4/2009 | Govindan et al. |
| 8,362,207 B2 | 1/2013 | Debinski et al. |
| 8,664,407 B2 | 3/2014 | Chen et al. |
| 2005/0002918 A1 | 1/2005 | Strauss et al. |
| 2006/0121539 A1 | 6/2006 | Debinski et al. |
| 2009/0123371 A1* | 5/2009 | Debinski .......... A61K 47/48246 424/1.69 |
| 2010/0209424 A1 | 8/2010 | Roopenian et al. |
| 2010/0291590 A1 | 11/2010 | Hartmann et al. |
| 2012/0039880 A1 | 2/2012 | Yan et al. |
| 2012/0041394 A1 | 2/2012 | Haider et al. |
| 2012/0209110 A1 | 8/2012 | Bankiewicz et al. |
| 2013/0012452 A1 | 1/2013 | Basiile et al. |
| 2013/0136692 A1 | 5/2013 | Debinski et al. |
| 2013/0209541 A1 | 8/2013 | Debinski et al. |

FOREIGN PATENT DOCUMENTS

| | | |
|---|---|---|
| WO | WO 2004069264 A1 | 8/2004 |
| WO | WO 2008112192 A | 9/2008 |

OTHER PUBLICATIONS

Carvalho et al. (Nature Neuroscience, 2006, 9(3): 322-330).*
Day B et al., EphA3 maintains tumorigenicity and is a therapeutic target in glioblastoma. Cancer Cell 2013 23: 238-428. Day B et al. Three distinct molecular surfaces in ephrin-A5 are essential for a functional interaction with EphA3. Journal of Biological Chemistry. Jul. 2005; 270(8): 26526-26532.
Nguyen et al. IL-13Rα2-Targeted Therapy Escapees: Biologic and Therapeutic Implications. Transl Oncol. Dec. 2011; 4(6):390-400.
Nguyen et al. A novel ligand delivery system to non-invasively visualize and therapeutically exploit the IL13Rα2 tumor-restricted biomarker. Neuro-Oncology. 2012; 14(10); 1230-1253.
Wykosky J et al. Interleukin-13 receptor α2, EphA2, and Fos-related antigen 1 as molecular denominators of high-grade astrocytomas and specific targets for combinatorial therapy. Clin Cancer Res. Jan. 2008;14(1):199-208.

(Continued)

*Primary Examiner* — Yan Xiao
(74) *Attorney, Agent, or Firm* — Myers Bigel, P.A.

(57) ABSTRACT

Provided herein is a construct comprising, in combination: an EphA3, EphA2 and/or EphB2 binding ligand; and at least one effector molecule. In some embodiments, the at least one effector molecule comprises a therapeutic agent, a nanoparticle, a detectable group, a lipid, or a liposome. In some embodiments, the construct is a fusion protein and/or a covalent conjugate. Further provided is a construct comprising in combination: a ligand that binds to EphA2, EphA3 and/or EphB2; a ligand that binds to IL-13Rα2; and at least one effector molecule. Also provided are methods of use thereof for treating cancer.

10 Claims, 12 Drawing Sheets

(56) References Cited

OTHER PUBLICATIONS

Davy A and Robbins SM. Ephrin-A5 modulates cell adhesion and morphology in an integrin-dependent manner. The EMBO Journal. 2000; 19(20): 5396-5405.
R&D Systems product description. Ephrin-A5: Products. www.rndsystems.com/product retrieved Nov. 7, 2013, 1 p.
Strausberg RL et al. Ephrin-A5 [*Homo sapiens*]. GenBank: AAH75054.1.www.ncbi.nlm.nih.gov/protein/AAH75054.1, 2 pp.
InvivoGen product descriptions. IgG-Fc engineering for therapeutic use. InvivoGen Insight . . . Apr./May 2006: 4 pp.
Wikipedia. Fragment crystallizable region. en.wikipedia.org/wiki/Fragment_crystallizable_region, retrieved May 29, 2014, 3 pp.
Immunogenetics product description. Antibody-dependent cellular cytotoxicity (ADCC) and Complement-dependent cytotoxicity(CDD).IMGT Lexique. www.imgt.org/IMGTeducaton/IMGTlexique/A/ADCC_and_CDC.html, retrieved May 29, 2014, 1 p.
Tanomand A et al. Protective properties of nontoxic recombinant exotoxin A (Domain I-II) against *Pseudomonas aeruginosa* infection. Iranian Journal of Biotechnology. Aug. 2013; 11(3): 193-8.
Mao W et al. EphB2 as a therapeutic antibody drug target for the treatment of colorectal cancer. Cancer Res. 2004; 64: 781-788.
Rath T et al. Fc-fusion proteins and FcRn: structural insights for longer-lasting and more effective therapeutics. Critical Reviews in Biotechnology. 2013: 20 pp.
Tandon M et al. Emerging strategies for EphA2 receptor targeting for cancer therapeutics. Expert Opin Ther Targets. Jan. 2011; 15(1): 31-51.
Di Gaetano N et al. Complement activation determines the therapeutic activity of rituximab in vivo. Journal of Immunology. Jul. 11, 2014; 171: 1581-1587.
Wikipedia. Antibody-dependent cell-mediated cytotoxicity. en.wikipedia.org/wiki/Antibody-dependent_cell-mediated_cytotoxicity, retrieved Jul. 11, 2014, 3 pp.
Clynes RA et al. Inhibitory Fc receptors modulate n vivo cytotoxicity against tumor targets. Nature Medicine. Apr. 2000; 6(4): 443-446.
Seidel UJ et al. Natural killer cell mediated antibody-dependent cellular cytotoxicity in tumor immunotherapy with therapeutic antibodies. Frontiers in Immunology. Mar. 27, 2013; 4: Article 76, 8 pp.
Courtois A et al. Complement dependent cytotoxicity activity of therapeutic antibody fragments is acquired by immunogenic glycan coupling. Electronic Journal of Biotechnology. Sep. 15, 2012; 15(5): 11 pp.
Nechansky A et al. Complement dependent cytotoxicity (CDC) activity of a humanized anti Lewis-Y antibody: FACS-based assay versus the 'classical' radioactive method—qualification, comparison and application of the FACS-based approach. Journal of Pharmaceutical and Biomedical Analysis. 2009; 49: 1014-1020.
Brenner BG et al. Role of antibody-dependent cellular cytotoxicity and lymphokine-activated killer cells in AIDS and related diseases. Journal of Leukocyte Biology. 1991; 50: 628-640.
Lamon EW et al. Antibody-dependent cell-mediated cytotoxicity in the Moloney sarcoma virus system: differential activity of IgG and IgM with different subpopulations of lymphocytes. The Journal of Experimental Medicine. 1977; 145: 302-313.
Miao H et al. EphA2 promotes infiltrative invasion of glioma stem cells in vivo through cross-talk with Akt and regulates stem cell properties. Oncogene advance online publication, Feb. 3, 2014; doi: 10.1038/onc.2013.590. Abstract only.
Weldon JE and Pastan I. A guide to taming a toxin: recombinant immunotoxins constructed from *Pseudomonas* exotoxin a for the treatment of cancer. FEBS J. Dec. 2011; 278(23): 4683-4700.
Pasquale EB. Eph receptors and ephrins in cancer: bidirectional signalling and beyond. Nature Reviews Cancer Mar. 2010; 10:165-180.
Beauchamp A and Debinski W. Ephs and Ephrins in Cancer: Ephrin-A1 Signaling. Semin Cell Dev Biol. Feb. 2012; 23: 109-115.
Ferluga A et al. Biological and structural characterization of glycosylation on ephrin-A1, a preferred ligand for EphA2 receptor tyrosine kinase. J Biol Chem; Jun. 21, 2013; 288(25):18448-57.
Wykosky J et al. A novel, potent, and specific ephrinAl-based cytotoxin against EphA2 receptor expressing tumor cells. Mol Cancer Ther. Dec. 2008; 6: 3208-3218.
Wykosky J et al. (2008) Soluble monomeric EphrinA1 is released from tumor cells and is a functional ligand for the EphA2 receptor. Oncogene; 27:7260-7273.
Nakada M et al. The phosphorylation of ephrin-B2 ligand promotes glioma cell migration and invasion. Int J Cancer. Mar. 2010; 126(5):1155-65.
Saikali S et al. Expression of nine tumour antigens in a series of human glioblastoma multiforme: interest of EGFRvIII, IL-13Ralpha2, gp100 and TRP-2 for immunotherapy. J.Neurooncol. Jan. 2007; 81(2):139-48.
Li W and Graeber MB. The molecular profile of microglia under the influence of glioma. Neuro-Oncol May 2014;14(8):958-978.
Ahmed Au et al. Understanding glioma stem cells: rationale, clinical relevance and therapeutic strategies. Expert Rev Neurother. May 2013; 13(5): 545-555.
Rycaj K and Tang Dg. Cancer stem cells and radioresistance. Int J Radiat Biol. Aug. 2014; 90(8): 615-621.
Juntilla MR and De Sauvage FJ. Influence of tumour microenvironment heterogeneity on therapeutic response. Nature. Sep. 19, 2013;501(7467):346-354.
Debinski W and Tatter SB. Convection-enhanced delivery for the treatment of brain tumors. Expert Rev Neurother . Oct. 2009;9(10):1519-27.
Kunwar S et al. Phase III randomized trial of CED of IL 13-PE38QQR vs Gliadel wafers for recurrent glioblastoma. Neuro Oncol. Aug. 2010;12(8):871-881.
Cloughesy TF et al. Glioblastoma: from molecular pathology to targeted treatment. Annu Rev Pathol. 2014;9:1-25. Abstract only.
Supplementary European Search Report and Opinion, EP 14860292, dated Jul. 5, 2017.
International Search Report and Written Opinion, PCT/US2014/064983, dated Mar. 10, 2015.
Smith FM et al. Dissecting the EphA3/Ephrin-A5 interactions using a novel functional mutagenesis screen. Journal of Biological Chemistry. Mar. 5, 2004; 279(10): 9522-9531.
Tomé CM et al. Structural and functional characterization of monomeric ephrinAl binding site to EphA2 receptor. Journal of Biological Chemistry. Apr. 20, 2012; 287(17): 14012-14022.
Himanen J-P et al. Repelling class discrimination: ephrin-A5 binds to and activates EphB2 receptor signaling. Nature Neuroscience. May 2004; 7(5); 501-509.
European Examination Report, EP 14860292, dated Mar. 7, 2018, 5 pages.

* cited by examiner

SEQUENCE LISTING

```
<160> NUMBER OF SEQ ID NOS: 31

<210> SEQ ID NO 1
<211> LENGTH: 14
<212> TYPE: PRT
<213> ORGANISM: Artificial
<220> FEATURE:
<223> OTHER INFORMATION: Amphipathic antimicrobial peptide sequence

<400> SEQUENCE: 1

Lys Leu Ala Lys Leu Ala Lys Lys Leu Ala Lys Leu Ala Lys
1               5                   10

<210> SEQ ID NO 2
<211> LENGTH: 14
<212> TYPE: PRT
<213> ORGANISM: Artificial
<220> FEATURE:
<223> OTHER INFORMATION: Amphipathic antimicrobial peptide sequence
```

```
<400> SEQUENCE: 2

Lys Leu Ala Lys Lys Leu Ala Lys Leu Ala Lys Lys Leu Ala
1               5                   10

<210> SEQ ID NO 3
<211> LENGTH: 14
<212> TYPE: PRT
<213> ORGANISM: Artificial
<220> FEATURE:
<223> OTHER INFORMATION: Amphipathic antimicrobial peptide sequence

<400> SEQUENCE: 3

Lys Ala Ala Lys Lys Ala Ala Lys Ala Ala Lys Lys Ala Ala
1               5                   10

<210> SEQ ID NO 4
<211> LENGTH: 14
<212> TYPE: PRT
<213> ORGANISM: Artificial
<220> FEATURE:
<223> OTHER INFORMATION: Amphipathic antimicrobial peptide sequence

<400> SEQUENCE: 4

Lys Leu Gly Lys Lys Leu Gly Lys Leu Gly Lys Lys Leu Gly
1               5                   10

<210> SEQ ID NO 5
<211> LENGTH: 16
<212> TYPE: PRT
<213> ORGANISM: Artificial
<220> FEATURE:
<223> OTHER INFORMATION: eA1 mutant sequence

<400> SEQUENCE: 5

Phe Gln Arg Phe Thr Pro Phe Thr Leu Gly Lys Glu Phe Lys Glu Gly
1               5                   10                  15

<210> SEQ ID NO 6
<211> LENGTH: 16
<212> TYPE: PRT
<213> ORGANISM: Artificial
<220> FEATURE:
<223> OTHER INFORMATION: eA5 mutant sequence

<400> SEQUENCE: 6

Phe Gln Leu Phe Thr Pro Phe Ser Leu Gly Phe Glu Phe Arg Pro Gly
1               5                   10                  15

<210> SEQ ID NO 7
<211> LENGTH: 7
<212> TYPE: PRT
<213> ORGANISM: Artificial
<220> FEATURE:
<223> OTHER INFORMATION: General targeting peptide sequence
<220> FEATURE:
<221> NAME/KEY: MISC_FEATURE
<222> LOCATION: (1)..(1)
<223> OTHER INFORMATION: Xaa is G or S
<220> FEATURE:
<221> NAME/KEY: MISC_FEATURE
<222> LOCATION: (2)..(2)
<223> OTHER INFORMATION: Xaa is Glu or Asp
<220> FEATURE:
<221> NAME/KEY: MISC_FEATURE
<222> LOCATION: (3)..(3)
<223> OTHER INFORMATION: Xaa is Met, Trp, Tyr or Ile
<220> FEATURE:
<221> NAME/KEY: MISC_FEATURE
```

<222> LOCATION: (4)..(4)
<223> OTHER INFORMATION: Xaa is Gly, Ser or Ala
<220> FEATURE:
<221> NAME/KEY: MISC_FEATURE
<222> LOCATION: (5)..(5)
<223> OTHER INFORMATION: Xaa is Trp, Phe, His or Tyr
<220> FEATURE:
<221> NAME/KEY: MISC_FEATURE
<222> LOCATION: (6)..(6)
<223> OTHER INFORMATION: Xaa is Val, Pro, Thr or Asn
<220> FEATURE:
<221> NAME/KEY: MISC_FEATURE
<222> LOCATION: (7)..(7)
<223> OTHER INFORMATION: Xaa is Arg, Lys or His

<400> SEQUENCE: 7

```
Xaa Xaa Xaa Xaa Xaa Xaa Xaa
1               5
```

<210> SEQ ID NO 8
<211> LENGTH: 14
<212> TYPE: PRT
<213> ORGANISM: Artificial
<220> FEATURE:
<223> OTHER INFORMATION: IL-13 receptor binding peptide sequence

<400> SEQUENCE: 8

```
Ala Cys Gly Glu Met Gly Trp Val Arg Cys Gly Gly Gly Ser
1               5                   10
```

<210> SEQ ID NO 9
<211> LENGTH: 9
<212> TYPE: PRT
<213> ORGANISM: Artificial
<220> FEATURE:
<223> OTHER INFORMATION: IL-13 receptor binding peptide sequence

<400> SEQUENCE: 9

```
Cys Gly Glu Met Gly Trp Val Arg Cys
1               5
```

<210> SEQ ID NO 10
<211> LENGTH: 7
<212> TYPE: PRT
<213> ORGANISM: Artificial
<220> FEATURE:
<223> OTHER INFORMATION: IL-13 receptor binding peptide sequence

<400> SEQUENCE: 10

```
Gly Glu Met Gly Trp Val Arg
1               5
```

<210> SEQ ID NO 11
<211> LENGTH: 7
<212> TYPE: PRT
<213> ORGANISM: Artificial
<220> FEATURE:
<223> OTHER INFORMATION: General targeting peptide sequence
<220> FEATURE:
<221> NAME/KEY: MISC_FEATURE
<222> LOCATION: (1)..(1)
<223> OTHER INFORMATION: Xaa is Leu, Ala, Ile, Val or Met
<220> FEATURE:
<221> NAME/KEY: MISC_FEATURE
<222> LOCATION: (2)..(2)
<223> OTHER INFORMATION: Xaa is Pro, Val, Thr or Asn
<220> FEATURE:
<221> NAME/KEY: MISC_FEATURE
<222> LOCATION: (3)..(3)
<223> OTHER INFORMATION: Xaa is Gln, Asn, Asp, Glu or His
<220> FEATURE:

```
<221> NAME/KEY: MISC_FEATURE
<222> LOCATION: (4)..(4)
<223> OTHER INFORMATION: Xaa is a hydrophobic amino acid (e.g. Leu, Ala,
      Ile, Val or Met)
<220> FEATURE:
<221> NAME/KEY: MISC_FEATURE
<222> LOCATION: (5)..(5)
<223> OTHER INFORMATION: Xaa is a Trp, Phe, His or Tyr
<220> FEATURE:
<221> NAME/KEY: MISC_FEATURE
<222> LOCATION: (6)..(6)
<223> OTHER INFORMATION: Xaa is Leu, Ala, Ile, Val or Met
<220> FEATURE:
<221> NAME/KEY: MISC_FEATURE
<222> LOCATION: (7)..(7)
<223> OTHER INFORMATION: Xaa is Phe, Trp, His or Tyr

<400> SEQUENCE: 11

Xaa Xaa Xaa Xaa Xaa Xaa Xaa
1               5

<210> SEQ ID NO 12
<211> LENGTH: 14
<212> TYPE: PRT
<213> ORGANISM: Artificial
<220> FEATURE:
<223> OTHER INFORMATION: IL-13 receptor binding peptide sequence

<400> SEQUENCE: 12

Ala Cys Leu Pro Gln Leu Trp Leu Phe Cys Gly Gly Gly Ser
1               5                   10

<210> SEQ ID NO 13
<211> LENGTH: 9
<212> TYPE: PRT
<213> ORGANISM: Artificial
<220> FEATURE:
<223> OTHER INFORMATION: IL-13 receptor binding peptide sequence

<400> SEQUENCE: 13

Cys Leu Pro Gln Leu Trp Leu Phe Cys
1               5

<210> SEQ ID NO 14
<211> LENGTH: 8
<212> TYPE: PRT
<213> ORGANISM: Artificial
<220> FEATURE:
<223> OTHER INFORMATION: IL-13 receptor binding peptide sequence

<400> SEQUENCE: 14

Leu Pro Gln Leu Trp Leu Phe Cys
1               5

<210> SEQ ID NO 15
<211> LENGTH: 7
<212> TYPE: PRT
<213> ORGANISM: Artificial
<220> FEATURE:
<223> OTHER INFORMATION: General targeting peptide sequence
<220> FEATURE:
<221> NAME/KEY: MISC_FEATURE
<222> LOCATION: (1)..(1)
<223> OTHER INFORMATION: Xaa is Ser or Gly
<220> FEATURE:
<221> NAME/KEY: MISC_FEATURE
<222> LOCATION: (2)..(2)
<223> OTHER INFORMATION: Xaa is Pro, Val, Thr or Asn
<220> FEATURE:
<221> NAME/KEY: MISC_FEATURE
<222> LOCATION: (3)..(3)
```

-continued

<223> OTHER INFORMATION: Xaa is Phe, Trp, His or Tyr
<220> FEATURE:
<221> NAME/KEY: MISC_FEATURE
<222> LOCATION: (4)..(4)
<223> OTHER INFORMATION: Xaa is Leu, Ala, Ile, Var or Met
<220> FEATURE:
<221> NAME/KEY: MISC_FEATURE
<222> LOCATION: (5)..(5)
<223> OTHER INFORMATION: Xaa is His, Trp, Phe or Tyr
<220> FEATURE:
<221> NAME/KEY: MISC_FEATURE
<222> LOCATION: (6)..(7)
<223> OTHER INFORMATION: Xaa is Leu, Ala, Ile, Var or Met

<400> SEQUENCE: 15

Xaa Xaa Xaa Xaa Xaa Xaa Xaa
1               5

<210> SEQ ID NO 16
<211> LENGTH: 14
<212> TYPE: PRT
<213> ORGANISM: Artificial
<220> FEATURE:
<223> OTHER INFORMATION: IL-13 receptor binding peptide sequence

<400> SEQUENCE: 16

Ala Cys Ser Pro Phe Leu His Leu Leu Cys Gly Gly Gly Ser
1               5                   10

<210> SEQ ID NO 17
<211> LENGTH: 9
<212> TYPE: PRT
<213> ORGANISM: Artificial
<220> FEATURE:
<223> OTHER INFORMATION: IL-13 receptor binding peptide sequence

<400> SEQUENCE: 17

Cys Ser Pro Phe Leu His Leu Leu Cys
1               5

<210> SEQ ID NO 18
<211> LENGTH: 7
<212> TYPE: PRT
<213> ORGANISM: Artificial
<220> FEATURE:
<223> OTHER INFORMATION: IL-13 receptor binding peptide sequence

<400> SEQUENCE: 18

Ser Pro Phe Leu His Leu Leu
1               5

<210> SEQ ID NO 19
<211> LENGTH: 7
<212> TYPE: PRT
<213> ORGANISM: Artificial
<220> FEATURE:
<223> OTHER INFORMATION: SV40 large T antigen nuclear localization
      sequence

<400> SEQUENCE: 19

Pro Lys Lys Lys Arg Lys Val
1               5

<210> SEQ ID NO 20
<211> LENGTH: 16
<212> TYPE: PRT
<213> ORGANISM: Artificial
<220> FEATURE:
<223> OTHER INFORMATION: Xenopus nucleoplasmin nuclear localization -continued

```
      sequence
<220> FEATURE:
<221> NAME/KEY: misc_feature
<222> LOCATION: (3)..(12)
<223> OTHER INFORMATION: Xaa can be any naturally occurring amino acid

<400> SEQUENCE: 20

Lys Arg Xaa Xaa Xaa Xaa Xaa Xaa Xaa Xaa Xaa Lys Lys Lys Leu
1               5                   10                  15

<210> SEQ ID NO 21
<211> LENGTH: 11
<212> TYPE: PRT
<213> ORGANISM: Artificial
<220> FEATURE:
<223> OTHER INFORMATION: Lysosomal localization signal sequence

<400> SEQUENCE: 21

Arg Lys Arg Ser His Ala Gly Tyr Gln Thr Ile
1               5                   10

<210> SEQ ID NO 22
<211> LENGTH: 23
<212> TYPE: PRT
<213> ORGANISM: Artificial
<220> FEATURE:
<223> OTHER INFORMATION: Lysosomal localization signal sequence

<400> SEQUENCE: 22

Arg Leu Lys Arg Met Gln Ala Gln Pro Pro Gly Tyr Arg His Val Ala
1               5                   10                  15

Asp Gly Glu Asp His Ala Val
            20

<210> SEQ ID NO 23
<211> LENGTH: 20
<212> TYPE: PRT
<213> ORGANISM: Artificial
<220> FEATURE:
<223> OTHER INFORMATION: Lysosomal localization signal sequence

<400> SEQUENCE: 23

Arg Gly Gln Gly Ser Thr Asp Glu Gly Thr Ala Asp Glu Arg Ala Pro
1               5                   10                  15

Leu Ile Arg Thr
            20

<210> SEQ ID NO 24
<211> LENGTH: 18
<212> TYPE: DNA
<213> ORGANISM: Artificial
<220> FEATURE:
<223> OTHER INFORMATION: PCR primer

<400> SEQUENCE: 24
taaggatccc aggacccg                                                  18

<210> SEQ ID NO 25
<211> LENGTH: 20
<212> TYPE: DNA
<213> ORGANISM: Artificial
<220> FEATURE:
<223> OTHER INFORMATION: PCR primer

<400> SEQUENCE: 25
gtacaattgc ggtgtcatct                                                20
```

<210> SEQ ID NO 26
<211> LENGTH: 18
<212> TYPE: DNA
<213> ORGANISM: Artificial
<220> FEATURE:
<223> OTHER INFORMATION: PCR primer

<400> SEQUENCE: 26
taaggatccc aggacccg                                                 18

<210> SEQ ID NO 27
<211> LENGTH: 20
<212> TYPE: DNA
<213> ORGANISM: Artificial
<220> FEATURE:
<223> OTHER INFORMATION: PCR primer

<400> SEQUENCE: 27
gtacaattgc ggtgtcatct                                               20

<210> SEQ ID NO 28
<211> LENGTH: 36
<212> TYPE: DNA
<213> ORGANISM: Artificial
<220> FEATURE:
<223> OTHER INFORMATION: Cloning primer

<400> SEQUENCE: 28
aaacatatgc accatcacca tcaccatcag gacccg                             36

<210> SEQ ID NO 29
<211> LENGTH: 33
<212> TYPE: DNA
<213> ORGANISM: Artificial
<220> FEATURE:
<223> OTHER INFORMATION: Cloning primer

<400> SEQUENCE: 29
tttaagcttg tcctgagcct ccggtgtcat ctg                                33

<210> SEQ ID NO 30
<211> LENGTH: 27
<212> TYPE: DNA
<213> ORGANISM: Artificial
<220> FEATURE:
<223> OTHER INFORMATION: Cloning primer

<400> SEQUENCE: 30
tactaagctt tgacatgccc accgtgc                                       27

<210> SEQ ID NO 31
<211> LENGTH: 26
<212> TYPE: DNA
<213> ORGANISM: Artificial
<220> FEATURE:
<223> OTHER INFORMATION: Cloning primer

<400> SEQUENCE: 31
atcgaagctt gtttacccgg agacag                                        26

EPHA3 AND MULTI-VALENT TARGETING OF TUMORS

RELATED APPLICATIONS

This application is a 35 U.S.C. § 371 national phase entry of PCT Application PCT/US2014/064983, filed Nov. 11, 2014, and published in English on May 14, 2015, as International Publication No. WO 2015/070210, and which claims the benefit of U.S. Provisional Application No. 62/036,262, filed Aug. 12, 2014, and U.S. Provisional Application No. 61/902,568, filed Nov. 11, 2013, the disclosure of each of which is incorporated herein by reference in its entirety.

GOVERNMENT FUNDING

This invention was made with government support under grant number R01 CA139099 awarded by the National Institutes of Health. The United States government has certain rights in the invention.

STATEMENT REGARDING ELECTRONIC FILING OF A SEQUENCE LISTING

A Sequence Listing in ASCII text format, submitted under 37 C.F.R. § 1.821, entitled 9151-203WO_ST25.txt, 8,865 bytes in size, generated on Mar. 20, 2015, and filed via EFS-Web, is provided in lieu of a paper copy. This Sequence Listing is hereby incorporated by reference into the specification for its disclosures.

BACKGROUND

Glioblastoma multiforme (GBM), or "glioblastoma," is a high-grade astrocytoma representing the most common form of primary brain tumors. The successful treatment of patients with GBM is still a major challenge, and the median survival rate is 14.5 months after diagnosis (Stupp et al., Promising survival for patients with newly diagnosed glioblastoma treated with concomitant radiation plus temozolomide followed by adjuvant temozolomide. J Clin Oncol. 2002 Mar. 1; 20(5):1375-82; Stupp et al., Radiotherapy plus concomitant and adjuvant temozolomide for glioblastoma. N Engl J Med. 2005 Mar. 10; 352(10):987-96).

Most anti-cancer therapeutics have defined targets such as oncogenes, enzymes or DNA, which may be localized to distinct intra-cellular compartments like the nucleus, mitochondria or cytosol. However, determining which targets and targeting strategies to utilize in order to provide the most effective clinical treatment for cancers such as GBM remains a major challenge.

Such targets may include the Eph receptors. (Pasquale (2010) Eph receptors and ephrins in cancer: bidirectional signalling and beyond. Nature Reviews Cancer 10:165-180). Ephrin-A ligands generally bind promiscuously EphA receptors; however, EphA3 is specifically activated by ephrin-A5 (eA5). EphA3 activation regulates several physiological processes like cell adhesion, migration and cellular morphologic responses that have also been related to tumor growth, invasiveness and metastasis (Beauchamp and Debinski (2012) Ephs and Ephrins in Cancer: Ephrin-A1 Signaling. Semin Cell Dev Biol. 23:109-115). EphA3 is overexpressed in GBM, in particular on tumor-initiating cells (Day et al., EphA3 maintains tumorigenicity and is a therapeutic target in glioblastoma. Cancer Cell 2013 23: 238-428).

EA5 binds with high specificity also to the Eph receptor A2, inducing its down-regulation and degradation (Ferluga et al. (2012) Biological and structural characterization of glycosylation on ephrin-A1, a preferred ligand for EphA2 receptor tyrosine kinase. J Biol Chem; 288:18448-57). EphA2 is overexpressed in glioblastoma (GBM) tumor specimens when compared to normal brain and can be specifically targeted by an ephrin-A1 (eA1)-based cytotoxin, killing GBM cells expressing the receptor (Wykosky et al. (2005) EphA2 as a novel molecular marker and target in glioblastoma. Mol Cancer Res; 3:541-551; Wykosky et al. (2007) A novel, potent, and specific ephrinA1-based cytotoxin against EphA2 receptor expressing tumor cells. Mol Cancer Ther 6:3208-3218). EphA2 has been shown to be involved in GBM invasiveness (Miao et al. (2014) EpbA2 promotes infiltrative invasion of glioma stem cells in vivo through cross-talk with Akt and regulates stem cell properties. doi: 10.1038/onc.2013.590. [Epub ahead of print]).

Studies have also shown that eA1 is able to activate EphA2 in a monomeric form (Wykosky et al. (2008) Soluble monomeric EphrinA1 is released from tumor cells and is a functional ligand for the EphA2 receptor. Oncogene; 27:7260-7273). It can also be mutagenized to improve binding affinity (Lema Tome et al. (2012) Structural and functional characterization of the monomeric EphrinA1 binding site to the EphA2 receptor. J Biol Chem; 287:14012-22), and the glycosylation of the ligand promotes activation of the receptor, stabilizing the formation of heterotetramers on the cell membrane (Ferluga et al. (2012) Biological and structural characterization of glycosylation on ephrin-A1, a preferred ligand for EphA2 receptor tyrosine kinase. J Biol Chem; 288:18448-57).

EphB2 is also over-expressed in GBM cells, especially invasive ones, but not in normal brain (Nakada et al. (2010) The phosphorylation of ephrin-B2 ligand promotes glioma cell migration and invasion. 126(5): 1155-65).

Another target in cancers such as glioblastoma is the IL-13 receptor IL-13Rα2, which is expressed in >75% of GBM tumor specimens (Debinski et al. (1999) Receptor for interleukin 13 is a marker and therapeutic target for human high-grade gliomas. Clin Cancer Res. 5(5):985-90; Saikali et al. (2007) Expression of nine tumour antigens in a series of human glioblastoma multiforme: interest of EGFRvIII, IL-13Ralpha2, gp100 and TRP-2 for immunotherapy. J. Neurooncol. 81(2):139-48) and is characterized as a cancer/testes like antigen (Debinski et al. (2000) Molecular expression analysis of restrictive receptor for interleukin 13, a brain tumor-associated cancer/testis antigen. Mol Med. 2000 May; 6(5):440-9). IL-13Rα2 is believed to act as a decoy receptor (Bernard et al. (2001) Expression of interleukin 13 receptor in glioma and renal cell carcinoma: IL13Ralpha2 as a decoy receptor for IL13 1. Lab Invest 81(9):1223-31). It has been shown that the IL-13 ligand binds to the IL13Rα2 receptor and is internalized through receptor mediated endocytosis (Kawakami et al. (2001) The interleukin-13 receptor alpha2 chain: an essential component for binding and internalization but not for interleukin-13-induced signal transduction through the STAT6 pathway. Blood 97(9):2673-9; Debinski et al. (1995) Human glioma cells overexpress receptors for interleukin 13 and are extremely sensitive to a novel chimeric protein composed of interleukin 13 and pseudomonas exotoxin. Clin. Cancer Res. 1(11):1253-8). Thus, drugs attached to the IL-13 ligand can be internalized and delivered specifically inside the glioma cells. However, some glioblastoma cells are resistant to targeting of IL-13Rα2 (Nguyen et al. (2011) IL-13Rα2-Targeted Therapy Escapees: Biologic and Therapeutic Implications. Transl Oncol. 4(6):390-400).

SUMMARY

Provided herein according to some embodiments is a construct comprising, in combination: a ligand that binds EphA2, EphA3, and/or EphB2; and at least one effector molecule. In some embodiments, the at least one effector molecule comprises a therapeutic agent, a nanoparticle, a detectable group, a lipid, or a liposome. In some embodiments, the construct is a fusion protein and/or covalent conjugate.

Also provided is a construct comprising, in combination: a ligand that binds EphA2, EphA3, and/or EphB2; a ligand that binds IL13-Rα2; and at least one effector molecule. In some embodiments, the at least one effector molecule comprises a therapeutic agent, a nanoparticle, a detectable group, a lipid, or a liposome. In some embodiments, the construct is a fusion protein or covalent conjugate.

In some embodiments, the ligand that binds EphA2, EphA3, and/or EphB2 is eA5, a mutant of eA5, or an EphA2, EphA3, and/or EphB2 binding fragment thereof. In some aspects, the ligand is eA1, a mutant of eA1, or an EphA3 binding fragment thereof.

In some embodiments, the ligand that binds IL13-Rα2 is IL-13, a mutant of IL13, or an IL13-Rα2 binding fragment thereof.

In some embodiments, the at least one effector molecule comprises a *diphtheria* toxin or a *Pseudomonas* exotoxin A. In some embodiments, the at least one effector molecule comprises an amphipathic antimicrobial peptide. In some embodiments, the at least one effector molecule comprises a radiopharmaceutical or a chemotherapeutic agent.

In some embodiments, the construct further comprises: a cytosol localization element covalently coupled between said binding ligand and said at least one effector molecule; and optionally a subcellular compartment localization signal element covalently coupled between said binding ligand and said at least one effector molecule.

Also provided is a nucleic acid that encodes a protein or peptide construct as taught herein. Further provided is a host cell that contains a nucleic acid of the invention and expresses the encoded protein or peptide.

Still further provided are methods of treating cancer in a subject in need thereof, comprising administering to said subject a construct as taught herein in a treatment effective amount. In some embodiments, the cancer is selected from the group consisting of breast cancer, bladder cancer, pancreatic cancer, colorectal cancer, head and neck cancer, thyroid cancer, prostate cancer, melanoma, oliodendrogliomas, pilocytic astrocytomas, anaplastic astrocytomas, choroid-plexus papilloma, meningiomas, and gliomas.

Also provided are methods of detecting cells expressing EphA2, EphA3, and/or EphB2, comprising administering a construct as taught herein to a cell or group of cells and detecting a detectable group coupled to said construct.

Further provided are methods of delivering at least one effector molecule to a subcellular compartment of a cell of interest, comprising: contacting a construct as taught herein to a cell of interest under conditions in which said construct is internalized therein and said effector molecule is delivered to a subcellular compartment.

Still further provided is a polypeptide comprising a mutant eA5, or an EphA2, EphA3, and/or EphB2 binding fragment thereof. Also provided is a nucleic acid encoding a polypeptide comprising a mutant eA5, or an EphA2, EphA3 and/or EphB2 binding fragment thereof.

Also provided is the use of a construct as taught herein in a method of medical treatment, as well as the use of a construct as taught herein in the preparation of a medicament for the treatment of a cancer.

BRIEF DESCRIPTION OF THE DRAWINGS

FIG. 4A-4B. EphA3 and EphA2 partially co-localized within GBM tumor and both are highly over-expressed in GBM tumor cell lines. 4A: Immunofluorescent staining of EphA3 (red) and GFAP, CD31 and EphA2 (green) on frozen sections of BTCOE4443 human GBM specimen. Nuclei are stained with DAPI (blue). 4B: Western blot analysis of EphA3 and EphA2 in GBM primary cell lines compared to the tumor specimens they derived from.

FIG. 7A-7I presents schematics of exemplary cytotoxin constructs according to some embodiments. 7A: The structure of an IgG1. 7B: dimeric eA5 conjugated to Fc. 7C: eA5-Fc conjugate of (B) chemically conjugated to PE38QQR. Opposite arrows represent chemical conjugation. As drawn, there would be two molecules of PE38QQR conjugated to the eA5-Fc construct. 7D: an eA5-Fc- PE38QQR fusion protein in which PE38QQR extends from one of the Fc ends. 7E: Bivalent eA5M/IL-13M-Fc-PE38QQR fusion cytotoxin in which monomeric moieties of eA5M (mutant eA5) and IL-13M (mutant IL-13) serve as targeting ligands and PE38QQR as an effector. 7F: Bivalent eA5M/IL-13M-Fc-PE38QQR fusion cytotoxin in which eA5M is homo-dimeric and IL-13M is fused to the C-terminus of an Fc region; PE38QQR is an effector. 7G: As in (F), but one eA5M molecule switches the site with IL-13M (and may be eA5 or eA5M). 7H: As in (F), but CH2 or CH3 is deleted from Fc. 7I: Bivalent eA5M/IL-13M-Fc protein fusion cytotoxin in which eA5M is homo-dimeric and IL-13M is fused or conjugated to the C-terminus of one of the Fc chains, while part of domain 2 of PE (D2) is fused or conjugated to the other Fc chain. An effector such as WP744 (a doxorubicin analog) is conjugated to D2, e.g., through a sulfide bond. Filled triangle represents WP744. Closed small ovals represent hinge regions; thin straight lines represent disulfide bonds. Constructs B-D have been generated thus far.

DETAILED DESCRIPTION OF EMBODIMENTS

Figure 1A:
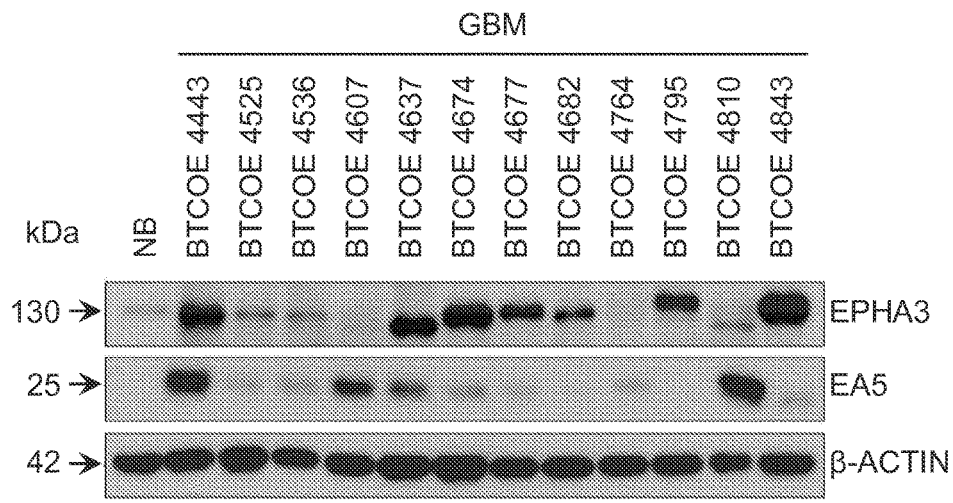
FIG. 1A-1B. EphA3 is overexpressed in GBM clinical specimens but not in normal brain. 1A: Western blot analysis of EphA3 and eA5 expression in 12 GBM human specimens compared to normal brain (NB). 1B: Western blot of EphA3 expression in gliomas and meningiomas.
Figure 1B:
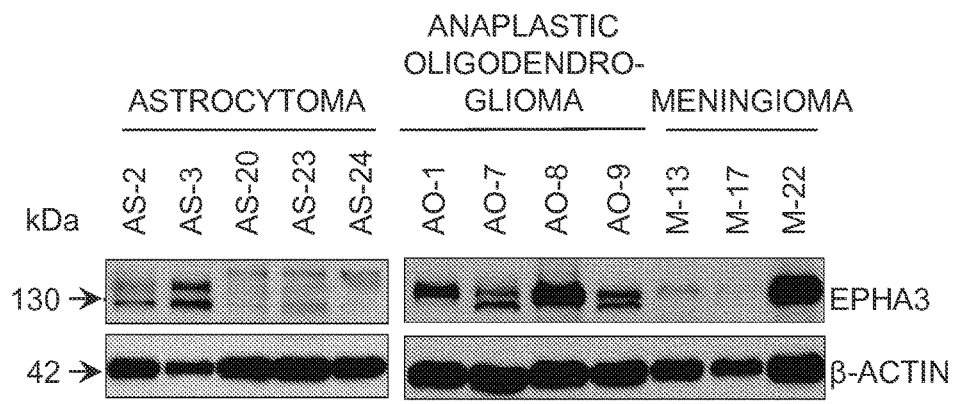
Figure 2:
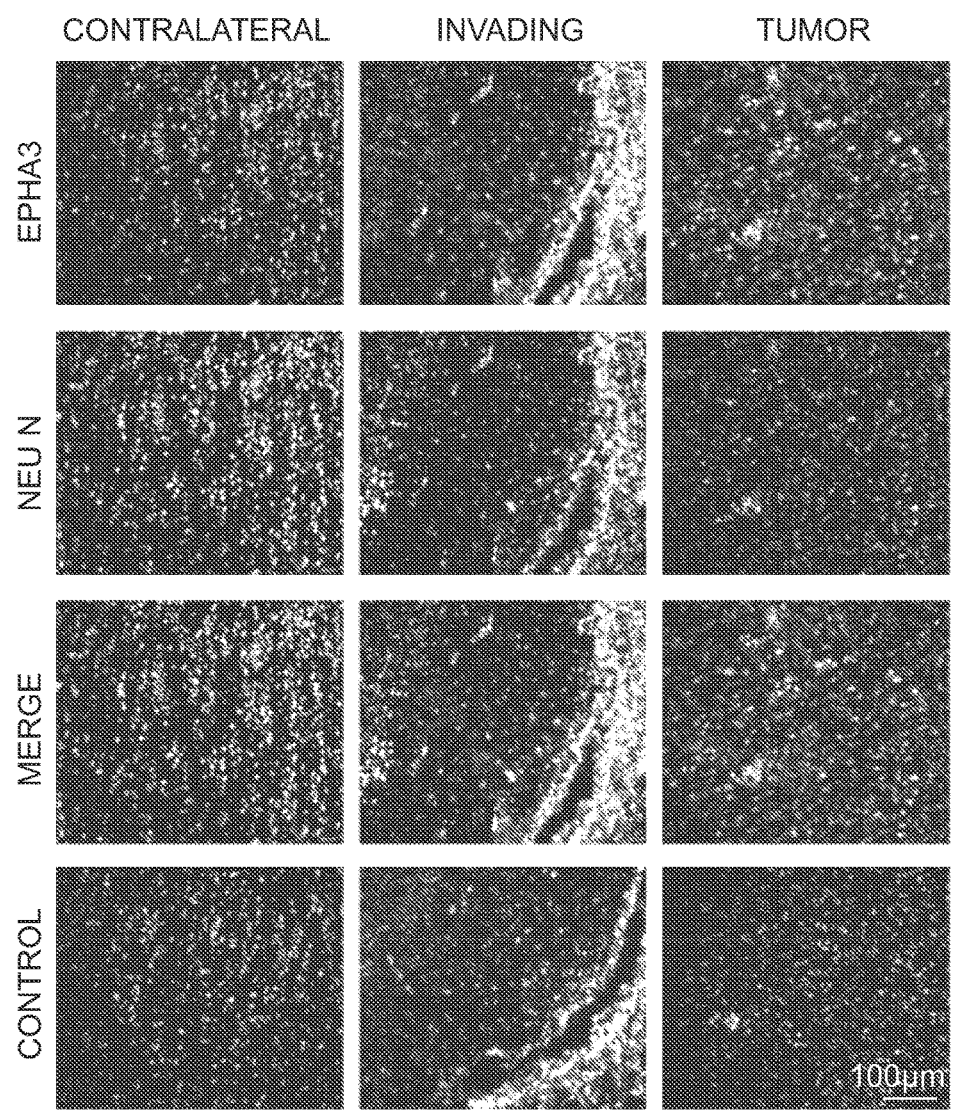
FIG. 2. EphA3 localized to the invading edge and in scattered areas of the tumor. Immunofluorescent staining of EphA3 (red) and NeuN (green) on the tumor, invading and contralateral area of the human brain 0204. Nuclei are stained with DAPI (blue).
Figure 3A:
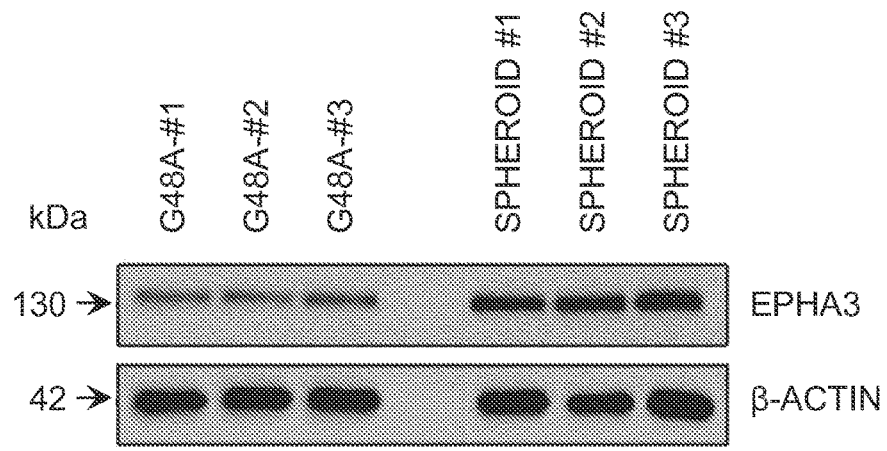
FIG. 3A-3B. EphA3 is overexpressed in GBM cells grown under spheroid culture condition and co-localizes with the glioma cancer stem cell marker Nestin. 3A: Western blot analysis of EphA3 expression in G48a GBM cell line grown under normal culture conditions (left) or under spheroid culture conditions (right). The experiment has been done in triplicate. 3B: Immunofluorescent staining of EphA3 (red) and Nestin (green) on a frozen section of BTCOE4443 human GBM specimen. Nuclei are stained with DAPI (blue).
Figure 3B:
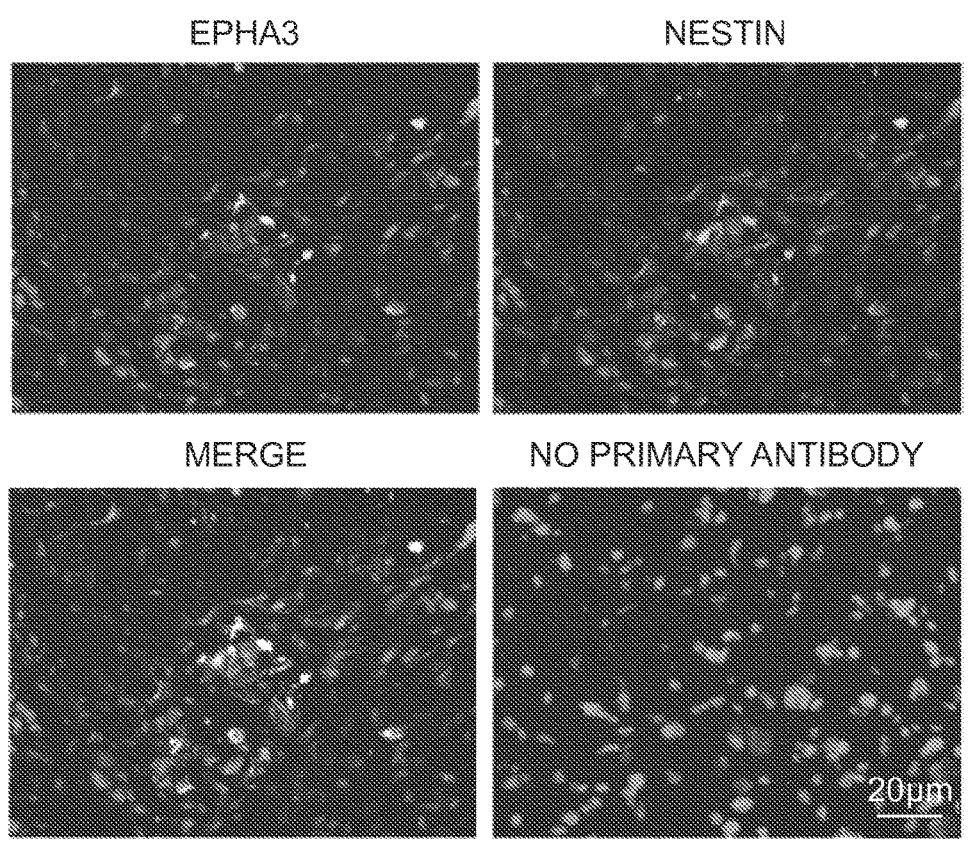
Figure 4A:
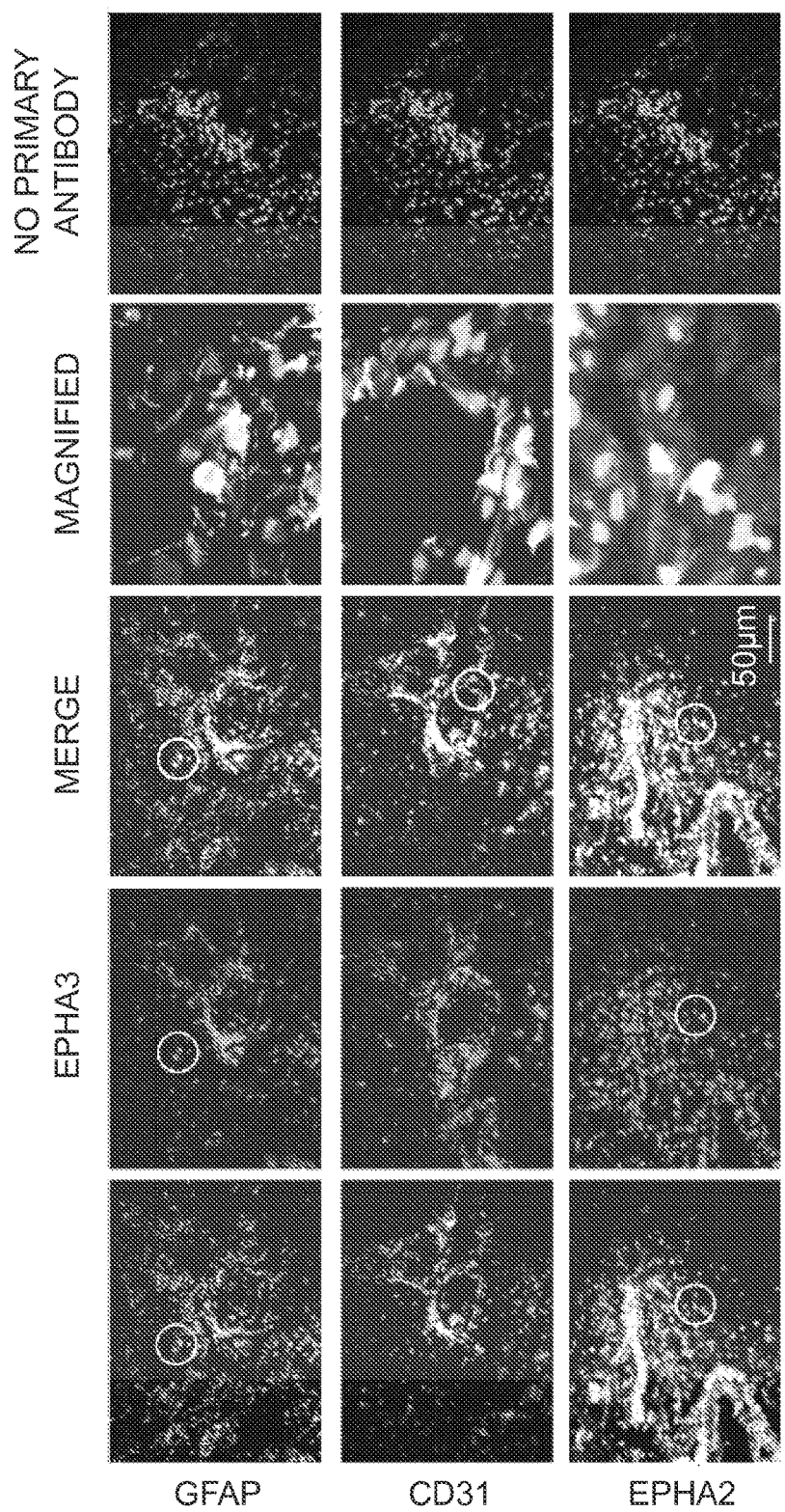
Figure 4B:
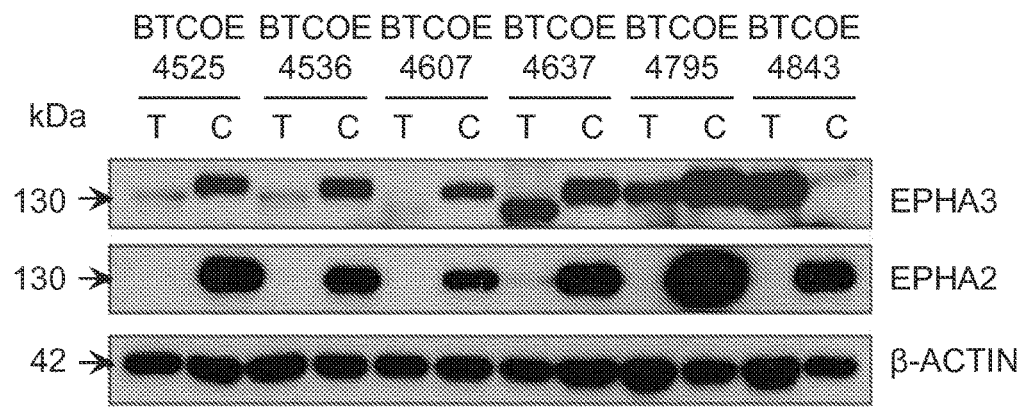
Figure 5A:
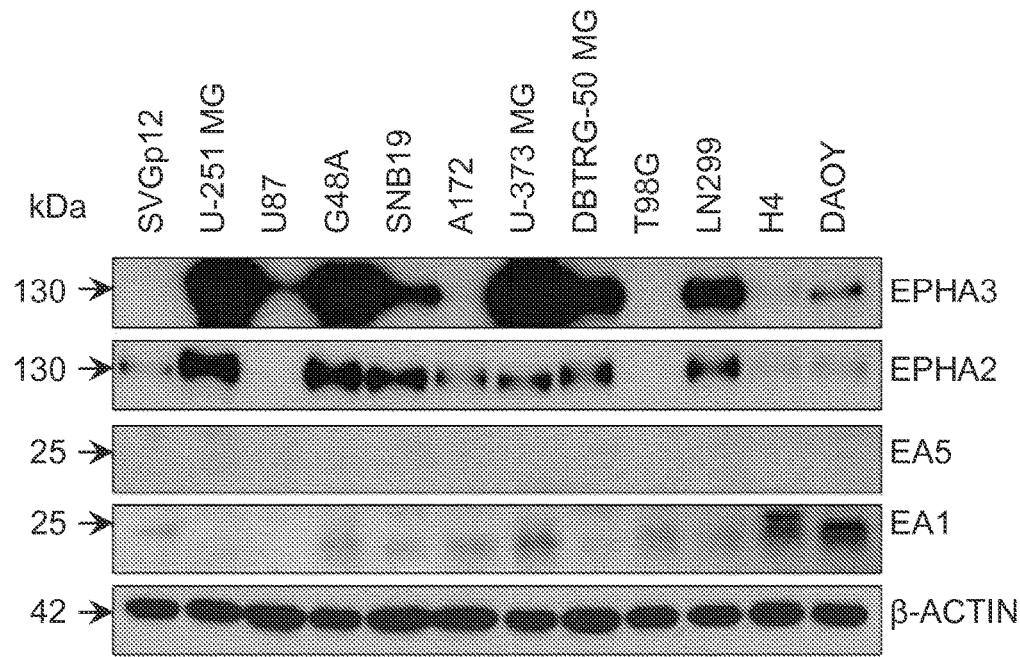
FIG. 5A-5C. EphA3 and EphA2 are overexpressed on several GBM cell lines compared to normal glial SVGp12 cells while their ligands are poorly expressed and localized to the membrane. 5A: Western Blot of EphA3 and EphA2 and their ligands, eA5 and eA1 respectively, on GBM cell lines and on SVG p12 glial cells. 5B: Immunofluorescent staining of EphA3 and EphA2 on GBM cells. Nuclei are stained with DAPI (blue). 5C: Flow cytometry analysis of EphA3 in U-251 MG and T98G GBM cell lines compared to the IgG control.
Figure 5B:
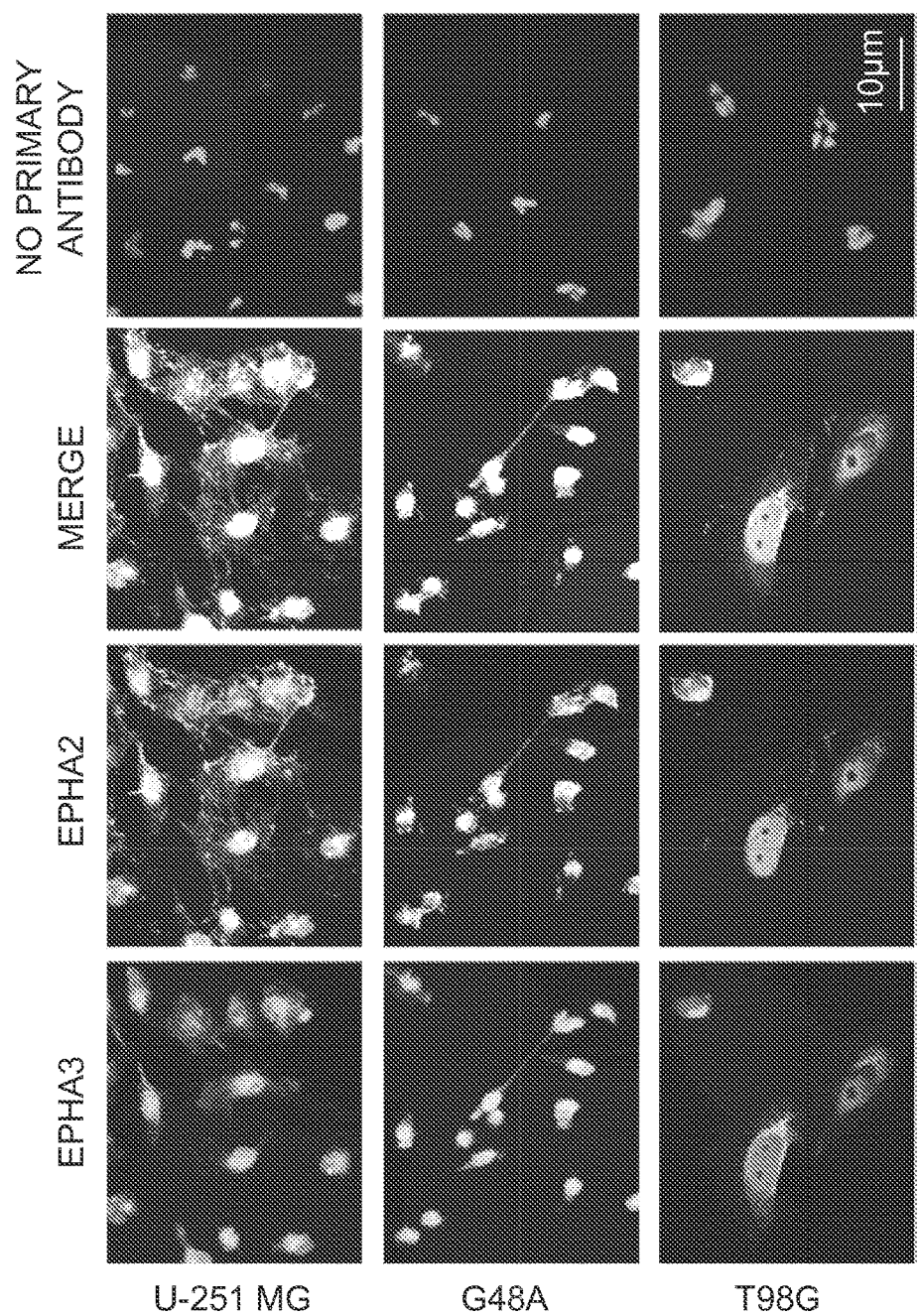
Figure 5C:
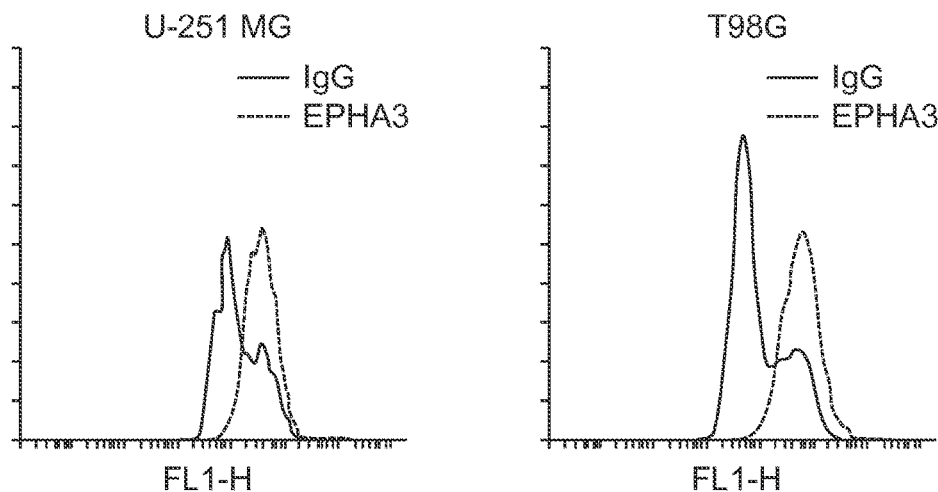
Figure 6A:
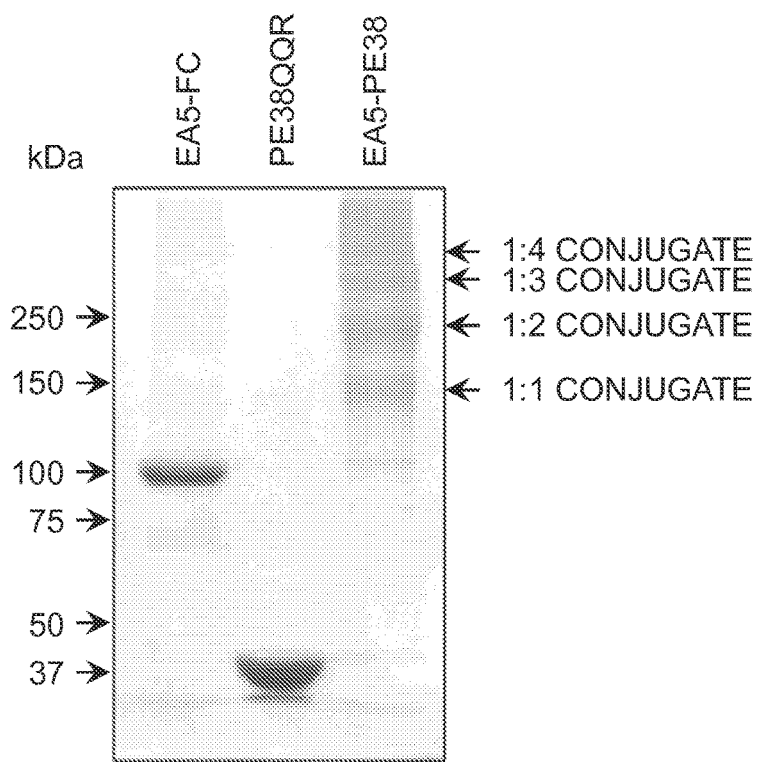
FIG. 6A-6E. eA5-PE38 cytotoxin kills GBM tumor cells specifically targeting both EphA3 and EphA2 receptors. 6A: SDS-PAGE of eA5-Fc produced in baculovirus, PE38QQR toxin produced in bacteria and then chemically conjugated cytotoxin eA5-PE38. 6B: Western blot analysis of EphA3 and EphA2 degradation following treatment with 1 µg/mL of eA5-Fc at the indicated time points on U-251 MG cells. 6C: Western blot of EphA3 and EphA2 on different GBM cell lines. 6D: Cell viability assay on GBM cell lines treated with the indicated concentrations of eA5-PE38 cytotoxin for 48 h or pretreated with eA5-Fc or cA1-Fc. 6E: Cell viability assay on GBM cell lines treated with the indicated concentrations of eA5-PE38 cytotoxin for 48 or 72 h.
Figure 6B:
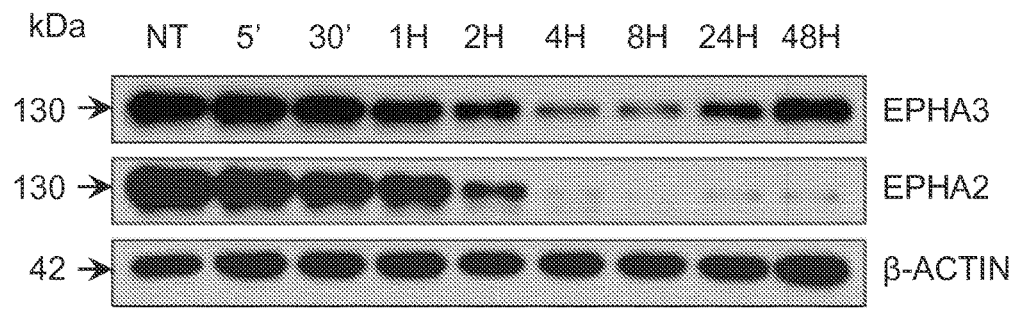
Figure 6C:
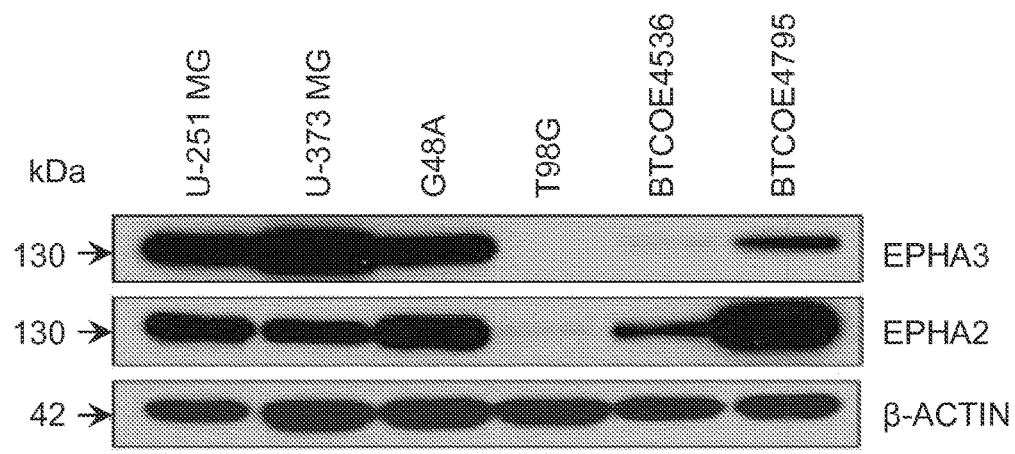
Figure 6D:
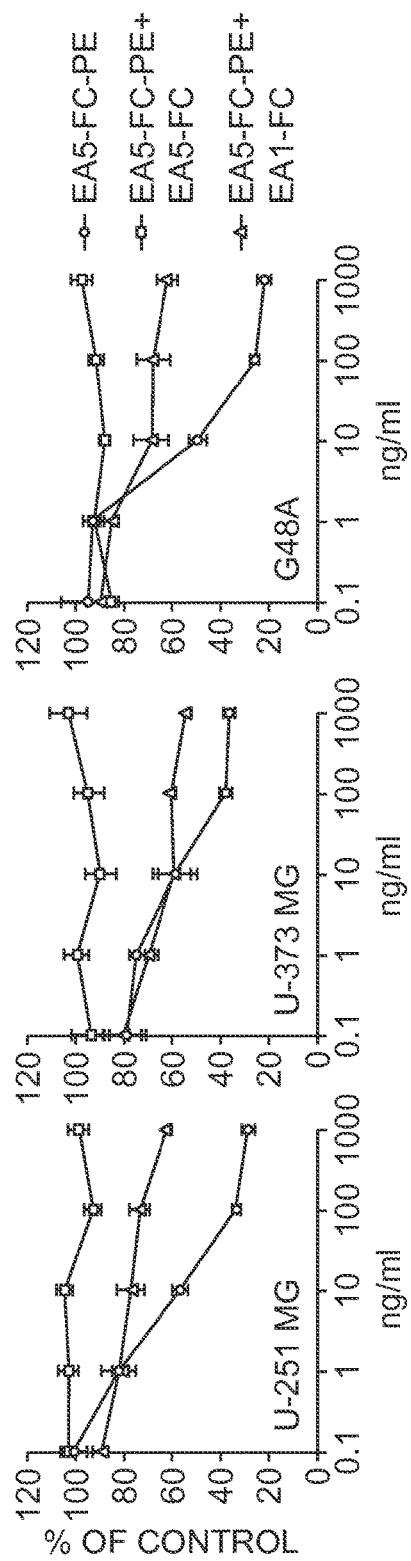
Figure 6E:
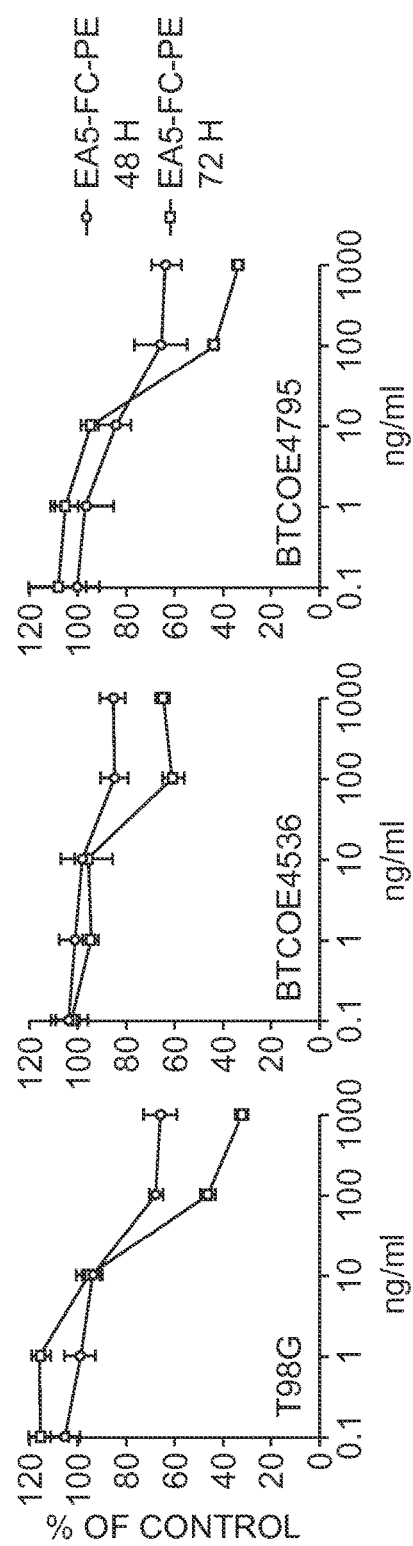

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the invention. Hence, the following specification is intended to illustrate some particular embodiments of the invention, but not to exhaustively specify all permutations, combinations and variations thereof.

The disclosures of all United States patent references cited herein are to be incorporated herein by reference to the extent they are consistent with the present disclosure.

Provided herein are constructs comprising a ligand that is useful in targeting EphA2, EphA3 and/or EphB2, and in some embodiments further targeting IL-13Rα2, providing in some embodiments a single therapeutic useful for target multiple sub-populations of receptor-overexpressing tumor cells and allowing targeting of different tumor compartments.

Glioblastoma (GBM) is the most common primary brain tumor in adults, with a median survival of only ~14.5 months. Interleukin 13 receptor alpha 2 (IL-13Rα2) and EPHA2 receptor are over-expressed in vast majority of patients with GBM, but not in normal brain, and also in spontaneous canine GBM, which is a faithful translational model of human disease. The first generation of an IL-13 based cytotoxin demonstrated objective clinical efficacy in patients with recurrent GBM.

The expression of IL-13Rα2 and EPHA2 is only partially overlapping, with the combined expression ~90% in patients with GBM. In further search for specific targets in GBM, the EPHA3 receptor was studied. It was found that EPHA3 was one of the most up-regulated genes in GBM cells cultured under neurosphere-forming conditions. Further, the expression of EPHA3 differs from that of EPHA2 in GBM to a great extent.

For example, all three of the receptors IL-13Rα2, EphA2 and EphA3 are expressed in tumor cells of the core of GBM tumors. IL-13Rα2 and EphA2 are present in tumor infiltrating cells, while mainly EphA2 is over-expressed in tumor neovasculature. IL-13Rα2, EphA2 and EphA3 were found to be associated with and to play crucial roles in pathobiology of glioma stem-like cells (GSC). IL-13Rα2 is highly present in cells isolated as GSCs from GBM and contributes to GBM cell stemness. Recent reports documented the critical roles of EphA2 and EphA3 in GSCs; both receptors have been shown to drive self-renewal and tumorigenicity of GSCs. And finally, the EphA3 receptor can be frequently detected in non-malignant cells of GBM, the infiltrating cells of monocytic origin.

Therefore, and without wishing to be bound by theory, EphA3, IL-13Rα2, EphA2, and EphB2 collectively are expressed in all GBM compartments believed to be involved in tumor progression and/or resistant to therapies. These compartments include the core of the tumor (main mass of the tumor), tumor infiltrating cells (which go out into other tissues), tumor neovasculature (abnormal vasculature, e.g., endothelial cells), glioma stem-like cells (having high malignancy), and/or non-malignant infiltrating cells of monocyte origin (immune cells such as monocytes, macrophages, T-cells).

Following this, provided herein according to some embodiments is a molecularly targeted construct useful in GBM treatment that (i) does not require patient pre-screening before treatment, (ii) attacks practically all important pathobiologically compartments of the tumor, and (iii) performs these functions in one molecular entity meaning that it will be suitable for monotherapy.

Furthermore, and without wishing to be bound by theory, multi-compartment targeting resulting in killing a larger portion of the tumor may serve to enhance the body's own immune response and promote tumor regression. See Lang et al., Neuro-oncology vo. 16, suppl 3, pp. iii39 (2014).

While the present discussion is focused in some aspects on the treatment of brain tumors such as glioblastoma, it will by understood by those in the art that many other cancers over-express IL-13RA2, EphA2, EphA3 and/or EPHB2, and thus the present invention is also useful in treating such other cancers.

A. DEFINITIONS

The terms "peptide," "polypeptide," and "protein" are used interchangeably and refer to any polymer of amino acids (dipeptide or greater) linked through peptide bonds.

In some embodiments, the peptides taught herein may comprise a capping group to improve resistance to degradation. See, e.g., US 2001/0143384 to Stensen et al. "Capping group" as used herein includes, but is not limited to, acetyl, benzoyl, formyl, trifluoroacetyl, benzyloxycarbonyl, tert-butyloxycarbonyl, biphenylylisopropyloxycarbonyl, triphenylmethyl, o-nitrobenzenesulfenyl, and diphenylphosphinyl. The capping groups may consist of such groups as $R^{10}CO-$, $R^{10}-O-CO-$, $R^{10}-PO-$, $R^{10}-SO_2-$ and arylalkyl-; where $R^{10}$ is selected from the group consisting of H, alkyl, alkenyl, alkynyl, aryl, and arylalkyl.

"Alkyl," as used herein, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. "Loweralkyl" as used herein, is a subset of alkyl and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like.

"Alkenyl," as used herein, refers to a straight or branched chain hydrocarbon containing from 2 to 10 carbons and containing at least one carbon-carbon double bond. Representative examples of "alkenyl" include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl and the like. "Lower alkenyl" as used herein, is a subset of alkenyl and refers to a straight or branched chain hydrocarbon group containing from 2 to 4 carbon atoms.

"Alkynyl," as used herein, refers to a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, 1-butynyl and the like. "Lower alkynyl" as used herein, is a subset of alkynyl and refers to a straight or branched chain hydrocarbon group containing from 2 to 4 carbon atoms.

The alkyl, alkenyl, and alkynyl groups of the invention can be substituted or unsubstituted unless otherwise specified. When substituted, the alkyl, alkenyl or alkynyl groups of the invention can be substituted with 1, 2, 3, 4, or 5 or more substituents independently selected from alkenyl, alkenyloxy, alkoxy, alkoxyalkoxy, alkoxycarbonyl, alkyl, alkylcarbonyl, alkylcarbonyloxy, alkylsulfinyl, alkylsulfonyl, alkylthio, alkynyl, aryl, azido, arylalkoxy, arylalkyl, aryloxy, carboxy, cyano, formyl, halogen, haloalkyl, haloalkoxy, hydroxy, hydroxyalkyl, mercapto, nitro, sulfamyl, sulfo, and sulfonate.

"Aryl" as used herein, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like.

The aryl groups of this invention can be substituted with 1, 2, 3, 4, or 5 or more substituents independently selected from alkenyl, alkenyloxy, alkoxy, alkoxyalkoxy, alkoxycarbonyl, alkyl, alkylcarbonyl, alkylcarbonyloxy, alkylsulfinyl, alkylsulfonyl, alkylthio, alkynyl, aryl, azido, arylalkoxy, arylalkyl, aryloxy, carboxy, cyano, formyl, halogen, haloalkyl, haloalkoxy, hydroxy, hydroxyalkyl, mercapto, nitro, sulfamyl, sulfo, and sulfonate.

"Arylalkenyl," as used herein, refers to an aryl group, as defined herein, appended to the parent molecular moiety through an alkenyl group, as defined herein. Representative examples of arylalkenyl include, but are not limited to, 2-phenylethenyl, 3-phenylpropen-2-yl, 2-naphth-2-ylethenyl, and the like, which may be substituted or unsubstituted as noted above.

"Recombinant" nucleic acid as used herein refers to a nucleic acid produced in vitro, e.g., by synthesis and/or by combining two or more nucleic acid sequences from different sources (e.g., a "heterologous" nucleic acid). The recombinant nucleic acid may be provided in the form of a "vector" or "delivery vector" in order to transform or transfect cells to contain the new nucleic acid. As used herein, a "vector" or "delivery vector" can be a viral or non-viral vector that is used to deliver a nucleic acid to a cell, tissue or subject.

A "recombinant" protein is a protein produced by a recombinant nucleic acid, often with the use of host cells. The nucleic acid may or may not be inserted into the genome of a host cell. The nucleic acid may exist, e.g., in plasmid form in a host cell. Alternatively, the recombinant protein may be produced by in vitro translation of the recombinant nucleic acid.

An "isolated" protein or polypeptide means a protein or polypeptide that is separated or substantially free from at least some of the other components of the naturally occurring organism or virus, for example, the cell or viral structural components or other proteins or nucleic acids commonly found associated with the protein. As used herein, the "isolated" protein or polypeptide is at least about 25%, 30%, 40%, 50%, 60%, 70%, 75%, 80%, 85%, 90%, 95%, 97%, 98%, 99% or more pure (w/w).

"Subjects" as used herein are generally human subjects and include, but are not limited to, cancer patients. The subjects may be male or female and may be of any race or ethnicity, including, but not limited to, Caucasian, African-American, African, Asian, Hispanic, Indian, etc. The subjects may be of any age, including newborn, neonate, infant, child, adolescent, adult, and geriatric. Subjects may also include animal subjects, particularly mammalian subjects such as canines, felines, bovines, caprines, equines, ovines, porcines, rodents (e.g. rats and mice), lagomorphs, primates (including non-human primates), etc., such as for veterinary medicine or pharmaceutical drug development purposes.

"Cancer" or "cancers" that can be detected and/or treated by the constructs, compositions and methods described herein include, but are not limited to, breast cancer, bladder cancer, pancreatic cancer, colorectal cancer, head and neck cancer, thyroid cancer, prostate cancer, melanoma, and brain cancer such as gliomas (e.g., GBM), etc.

Many cancers over-express IL-13Rα2 (e.g., GBM and other brain cancers, human pediatric brain tumors, brainstem glioma, renal cell carcinoma, squamous cell carcinoma of head and neck, ovarian cell carcinoma, pancreatic cancer, colorectal cancer, and melanoma), EphA2 (e.g., GBM and other brain cancer, breast cancer, prostate cancer, urinary bladder cancer, skin cancer, lung cancer, ovarian cancer, esophageal cancer, renal cancer, colon cancer and vulvar cancer), EphA3 (e.g., GBM and other brain cancers, leukemia, lymphoma, lung cancer, skin cancer and gastric carcinoma) and/or EphB2 (e.g., GBM and other brain cancers, gastric cancer, colon cancer, neuroblastomas, small cell lung carcinoma, and melanoma). This expression may have concomitant presence in various tumor compartments.

"Brain cancer" or "brain tumor" may be of any stage, grade, histomorphological feature, invasiveness, aggressivity or malignancy of an affected tissue or cell aggregation in any part of the central nervous system (i.e., brain and spinal cord). In some embodiments, the brain tumor is a glioma. In some embodiments, the tumor is an anaplastic astrocytoma, anaplastic oligoastrocytoma or anaplastic oligodendroglioma, in particular, fibrillary astrocytoma WHO grade II, oligoastrocytoma WHO grade II, oligodendroglioma grade II, anaplastic astrocytoma WHO grade III, anaplastic oligoastrocytoma WHO grade II, anaplastic oligodendroglioma grade III or glioblastoma multiforme (see, e.g., US Patent Application Publication No. 2010/0291590).

Gliomas are tumors occurring in the glial cells, which help support and protect critical areas of the brain. Gliomas are the most common type of brain tumor in adults, responsible for about 42% of all adult brain tumors. Gliomas are further characterized by the types of cells they affect, into the categories of astrocytoma (affecting astrocytes), oligodendroglioma (affecting oligodendrocytes), ependymoma (affecting ependymal cells), meningiomas (affecting the meninges), acoustic neuroma/schwannoma (affecting Schwann's cells), and medulloblastoma (affective cells in the cerebellum). See also U.S. 2013/0012452 to Basile et al.

Astrocytomas are graded from I to IV depending on the speed of progression. Grade I (pilocytic astrocytoma) is slow growing, with little tendency to infiltrate surrounding brain tissue. Grade II (diffuse astrocytoma) is fairly slow-growing, with some tendency to infiltrate surrounding brain tissue. Grade III (anaplastic/malignant astrocytoma) tumors grow rather quickly and infiltrate surrounding brain tissue. Grade IV (glioblastoma or "GBM") is an extremely aggressive and lethal form of brain cancer. Unfortunately, it is the most common form of brain tumor in adults, accounting for about 67% of all astrocytomas.

Oligodendrogliomas, which make up 4% of brain tumors, mostly affect people over 45 years of age. Some subtypes of this tumor are particularly sensitive to treatment with radiation therapy and chemotherapy. Half of patients with oligodendrogliomas are still alive after five years.

Ependymomas are rare; about 2% of all brain tumors, but are the most common brain tumor in children. They generally do not affect healthy brain tissue and do not spread beyond the ependyma. Although these tumors respond well to surgery, particularly those on the spine, ependymomas cannot always be completely removed. The five-year survival rate for patients over age 45 approaches 70%.

Meningiomas affect the meninges, the tissue that forms the protective outer covering of the brain and spine. One-quarter of all brain and spinal tumors are meningiomas, and up to 85% of them are benign.

Malignant gliomas are a fatal disease with an average life-expectancy following diagnosis of less than one year. The prognosis for patients with high-grade gliomas is very poor, and is especially so for older patients. Of Americans diagnosed each year with malignant gliomas, about half are alive 1 year after diagnosis, and 25% after two years. Those with anaplastic astrocytoma survive about three years. Glioblastoma has the worst prognosis, with a life expectancy of less than 9-15 months following diagnosis.

"Effector molecule" as used herein includes therapeutic agents, nanoparticles, detectable groups, targeting ligands, and delivery vehicles (e.g., antibodies, lipids, liposomes). See, e.g., U.S. Pat. No. 6,630,576.

"Therapeutic agent" as used herein may be any therapeutic agent including, but not limited to, genetic materials or agents, radionuclides, chemotherapeutic agents, and cytotoxic agents (See, e.g., U.S. Pat. No. 6,949,245 to Sliwkowski), and amphipathic antimicrobial peptides. Other exemplary therapeutic agents include, but are not limited to, radiopharmaceuticals, including, but not limited to Auger electrons, chemotherapeutic agents incorporating a radionuclide, and photosensitizers.

"Radionuclide" as described herein includes, but is not limited to, $^{227}$Ac, $^{211}$At, $^{131}$Ba, $^{77}$Br, $^{109}$Cd, $^{51}$Cr, $^{67}$Cu, $^{165}$Dy, $^{155}$Eu, $^{153}$Gd, $^{198}$Au, $^{166}$Ho, $^{113m}$In, $^{115m}$In, $^{123}$I, $^{125}$I, $^{131}$I, $^{189}$Ir, $^{191}$Ir, $^{192}$Ir, $^{194}$Ir, $^{52}$Fe, $^{55}$Fe, $^{59}$Fe, $^{177}$Lu, $^{109}$Pd, $^{32}$P, $^{226}$Ra, $^{186}$Re, $^{188}$Re, $^{153}$Sm, $^{46}$Sc, $^{47}$Sc, $^{72}$Se, $^{75}$Se, $^{105}$Ag, $^{89}$Sr, $^{35}$S, $^{177}$Ta, $^{117m}$Sn, $^{121}$Sn, $^{166}$Yb, $^{169}$Yb, $^{90}$Y, $^{212}$Bi, $^{119}$Sb, $^{197}$Hg, $^{97}$Ru, $^{100}$Pd, $^{100m}$Rh, and $^{212}$Pb.

"Chemotherapeutic agent" as used herein includes, but is not limited to, methotrexate, daunomycin, mitomycin C, cisplatin, vincristine, epirubicin, fluorouracil, verapamil, cyclophosphamide, cytosine arabinoside, aminopterin, bleomycin, mitomycin C, democolcine, etoposide, mithramycin, chlorambucil, melphalan, daunorubicin, doxorubicin, tamosifen, paclitaxel, vincristin, vinblastine, camptothecin, actinomycin D, and cytarabine. Other examples are found in U.S. Patent Application Publication 2006/0121539 (Debinski et al.), which is incorporated by reference herein in its entirety. Other exemplary chemotherapeutic agents include topoisomerase I inhibitors, such as camptothecins (e.g., topotecan and irinotecan) and indenoisoquinolines (e.g., indotecan and indimitecan).

"Cytotoxic agent" or "toxic agent" as used herein includes, but is not limited to, maytansinoids and maytansinoid analogs, taxoids, CC-1065 and CC-1065 analogs, dolastatin and dolastatin analogs, ricin (or more particularly the ricin A chain), aclacinomycin, *Diphtheria* toxin, Monensin, Verrucarin A, Abrin, Tricothecenes, and *Pseudomonas* exotoxin A, taxol, cytochalasin B, gramicidin D, ethidium bromide, emetine, mitomycin, etoposide, tenoposide, antimitotic agents, such as the vinca alkaloids (e.g., vincristine and vinblastine), colchicin, anthracyclines, such as doxorubicin (inclusive of 4'-O-benzylated Dox analogs WP744 and WP769) and daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof, antimetabolites (e.g., methotrexate, 6-mercaptopurine, 6-thioguanine, cytarabine, and 5-fluorouracil decarbazine), alkylating agents (e.g., mechlorethamine, thioepa chlorambucil, meiphalan, carmustine (BSNU), lomustine (CCNU), cyclothosphamide, busulfan, dibromomannitol, streptozotocin, mitomycin C, and cis-dichlorodiamine platinum (II) (DDP)), and antibiotics, including, but not limited to, dactinomycin (formerly actinomycin), bleomycin, mithramycin, calicheamicin, and anthramycin (AMC).

In some embodiments, cytotoxic agents include toxins such as *Pseudomonas* exotoxin, ricin, abrin, ribonuclease (RNase), DNase I, Staphylococcal enterotoxin-A, pokeweed antiviral protein, gelonin, *diphtheria* toxin, etc. See, e.g., U.S. Pat. No. 7,517,964. In some embodiments, *Pseudomonas* exotoxin or a *Diphtheria* toxin is preferred. See U.S. Pat. No. 5,328,984 to Pastan et al. and U.S. Pat. No. 6,296,843 to Debinski, which are each incorporated by reference herein in its entirety. *Pseudomonas* exotoxins can include, but are not limited to, *Pseudomonas* exotoxin A (PE). The *Pseudomonas* exotoxin can be modified such that it substantially lacks domain Ia, and in some embodiments *Pseudomonas* exotoxins include PE38QQR and PE4E. *Diphtheria* toxins can include DT390, a *diphtheria* toxin in which the native binding domain is eliminated. It will be appreciated that in various embodiments, the therapeutic agents can be attached to, e.g., the amino terminus or the carboxyl terminus.

"Amphipathic antimicrobial peptide" as used herein includes amphipathic peptides that induce apoptosis of cancer cells, presumably through their ability to depolarize mitochondrial membranes. K. Rege et al., *Cancer Res.* 67, 6368 (Jul. 1, 2007). Such peptides are, in general, from 10, 12 or 13 to 20, 30 or 40 amino acids in length, or more, and typically have an amphipathic alpha-helical structure. Examples include, but are not limited to, (KLAKLAK)$_2$ (SEQ ID NO:1); (KLAKKLA)$_2$ (SEQ ID NO:2) (KAAKKAA)$_2$ (SEQ ID NO:3) and (KLGKKLG)$_2$ (SEQ ID NO:4). See, e.g., Ruoslahti et al., U.S. Patent Application Publication No. 2001/0046498 (Nov. 29, 2001).

"Nanoparticle" as used herein includes particles that are about 0.5 to about 1,000 nanometers in size and may include natural and/or synthetic moieties. In some embodiments, the nanoparticle crosses the blood brain barrier. In some embodiments, the nanoparticle may incorporate a therapeutic agent. See, e.g., U.S. Pat. No. 8,535,726 to Dai et al.; U.S. Pat. No. 8,252,338 to Forte et al.; U.S. Pat. No. 8,246,968 to Zale et al.; U.S. 2013/0122056 to Zhang et al. In some embodiments, the nanoparticle comprises a polymeric matrix, which may comprises two or more polymers. Polymers of the matrix may include, e.g., polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, or combinations thereof. In some embodiments, the polymeric matrix comprises one or more polyesters, polyanhydrides, polyethers, polyurethanes, polymethacrylates, polyacrylates or polycyanoacrylates. In some embodiments, at least one polymer is a polyalkylene glycol. In some embodiments, the polyalkylene glycol is polyethylene glycol. In some embodiments, at least one polymer is a polyester. In some embodiments, the polyester is selected from the group consisting of PLGA, PLA, PGA, and polycaprolactones. In some embodiments, the polyester is PLGA or PLA. In some embodiments, the polymeric matrix comprises a copolymer of two or more polymers, such as a copolymer of a polyalkylene glycol and a polyester. In some embodiments, the copolymer is a copolymer of PLGA or PLA and PEG. In some embodiments, the polymeric matrix comprises PLGA or PLA and a copolymer of PLGA or PLA and PEG.

"Detectable group" or "label" as used herein includes, but is not limited to, radiolabels (e.g., $^{35}S$, $^{125}I$, $^{32}P$, $^{3}H$, $^{14}C$, $^{131}I$), enzyme labels (e.g., horseradish peroxidase, alkaline phosphatase), gold beads, chemiluminescence labels, ligands (e.g., biotin, digoxin) and/or fluorescence labels (e.g., rhodamine, phycoerythrin, fluorescein, fluorescent proteins), a fluorescent protein including, but not limited to, a green fluorescent protein or one of its many modified forms, a nucleic acid segment in accordance with known techniques, and energy absorbing and energy emitting agents. Thus "label" or "detectable group" as used herein may be any suitable label or detectable group detectable by spectroscopic, photochemical, biochemical, immunochemical, electrical, optical or chemical means, including, but not limited to, biotin, fluorophores, antigens, porphyrins, and radioactive isotopes. Labels useful in the present invention include biotin for staining with labeled avidin or streptavidin conjugate, magnetic beads (e.g., Dynabeads™), fluorescent dyes (e.g., fluorescein, fluorescein-isothiocyanate [FITC], Texas red, rhodamine, green fluorescent protein, enhanced green fluorescent protein, lissamine, phycoerythrin, Cy2, Cy3, Cy3.5, Cy5, Cy5.5, Cy7, FluorX [Amersham], SyBR Green I & II [Molecular Probes], and the like), radiolabels (e.g., $^{3}H$, $^{35}S$, $^{14}C$, or $^{32}P$), enzymes (e.g., hydrolases, particularly phosphatases such as alkaline phosphatase, esterases and glycosidases, or oxidoreductases, particularly peroxidases such as horseradish peroxidase, and the like), substrates, cofactors, inhibitors, chemiluminescent groups, chromogenic agents, and calorimetric labels such as colloidal gold or colored glass or plastic (e.g., polystyrene, polypropylene, latex, etc.) beads.

"Treat," "treating" or "treatment" as used herein refers to any type of treatment that imparts a benefit to a patient afflicted with a disease, including improvement in the condition of the patient (e.g., in one or more symptoms), delay in the progression of the disease, reduction in tumor volume or invasiveness, lengthening of average life expectancy, etc.

"Pharmaceutically acceptable" as used herein means that the construct or composition is suitable for administration to a subject to achieve the treatments described herein, without unduly deleterious side effects in light of the severity of the disease and necessity of the treatment.

"Concurrently administering" or "concurrently administer" as used herein means that the two or more constructs and/or compositions are administered closely enough in time to produce a combined effect (that is, concurrently may be simultaneously, or it may be two or more events occurring within a short time period before or after each other, e.g., sequentially). Simultaneous concurrent administration may be carried out by mixing the constructs and/or compositions prior to administration, or by administering the constructs and/or compositions at the same point in time but at different anatomic sites and/or by using different routes of administration.

"Internalizing factor" as used herein may be any construct that binds to a cell surface protein which is then taken up into the cell by binding. Numerous such internalizing factors are known, including but not limited to those described in D. Curiel et al., U.S. Pat. Nos. 6,274,322 and 6,022,735, the disclosures of which are incorporated herein by reference.

B. LIGANDS THAT BIND TO EPHA3, EPHA2 AND/OR EPHB2

In some embodiments of the invention, ligands that specifically bind EphA3, EphA2 and/or EphB2 are peptides. In some embodiments, the agent is eA5 or a fragment thereof that specifically binds EphA3, EphA2 and/or EphB2. In some embodiments, the ligand is eA1 or a fragment thereof that specifically binds EphA3 and/or EphA2. EA5 and eA1 are each known and may be produced recombinantly using techniques known in the art. However, unlike eA1, eA5 has an advantage of binding both EphA2 and EphA3 receptors and also the EphB2 receptor, which is expressed on malignant cells and takes part in the control of glioma cell invasion.

One of skill in the art will appreciate that analogues or fragments of eA5 or eA5 mutants may also specifically bind to EphA3 and/or EphA2. For example, conservative substitutions of residues (e.g., a serine for an alanine or an aspartic acid for a glutamic acid) comprising native eA5 may provide eA5 analogues that also specifically bind to EphA3. Thus, the terms "eA5" or "eA5 mutant" when used in reference to a targeting molecule, also includes fragments, analogues or peptide mimetics of eA5 or eA5 mutants that also specifically bind to one or more of the EphA3, EphA2 and EphB2 receptors.

Similarly, one of skill in the art will appreciate that analogues or fragments of eA1 or eA1 mutants may specifically bind to EphA3 and/or EphA2. For example, conservative substitutions of residues (e.g., a serine for an alanine or an aspartic acid for a glutamic acid) comprising native eA1 may provide eA1 analogues that also specifically bind to EphA3. Thus, the terms "eA1" or "eA1 mutant" when used in reference to a targeting molecule, also includes fragments, analogues or peptide mimetics of eA1 or eA1 mutants that also specifically bind to one or more of the EphA3 and EphA2 receptors.

In some embodiments, the targeting peptide is in monomeric form. In some embodiments, the targeting peptide is in dimeric form. Dimers may be formed using methods known in the art, e.g., with an Fc fusion protein or hinge linker. See, e.g., U.S. 2010/0209424 to Roopenian et al. and U.S. 2012/0039880 to Yan et al., which are incorporated by reference herein.

In some embodiments, the agent is a glycosylated form of eA1 or eA5, mutants or fragments thereof. See Ferluga et al., J Biol Chem 288(25):18448-18457 (2013).

In some embodiments, the eA5 or eA1 mutant is a G-H loop mutant, such as $^{108}$FQRFTPFTLGKEFKEG$^{123}$ (SEQ ID NO:5) of eA1 (UniProtKB/Swiss-Prot Accession No. P20827.2) or $^{118}$FQLFTPFSLGFEFRPG$^{133}$ (SEQ ID NO:6) of eA5 (UniProtKB/Swiss-Prot Accession No. P52803.1). See Lema Tome et al., J Biol Chem 287:14012-14022 (2012). In some embodiments, the mutation is at amino acid 109 (Q), 113 (P), 115 (T), 117 (0), 122 (E), or any combination thereof, of eA1. In some embodiments, the mutation is at P113, T115, G117 or E122 of eA1, and the wild-type amino acid is substituted with an alanine (A). In some embodiments, the mutation is at amino acid 119 (Q), 123 (P), 125 (S), 127 (G), 132 (P), or any combination thereof, of eA5. In some embodiments, the mutation is at P123, S125, G127 or P132 of eA5, and the wild-type amino acid is substituted with A. In some embodiments, the eA1 or eA5 mutant may have more than one, two or even three or more, amino acid changes.

In some embodiments, the eA5 or eA1 mutant has an enhanced binding affinity for EphA2, EphA3 and/or EphB2, in addition to enhanced binding affinity to EphA2, as compared to the corresponding wild-type eA1 or eA5 binding affinity.

The targeting peptides of the present invention can be coupled to or conjugated to one or more effector molecules, cytosol localization elements, and/or subcellular compartment localization signal elements by any suitable technique, including those described further below.

The described constructs can be used for therapeutic and/or diagnostic purposes.

C. LIGANDS THAT BIND TO IL-13α2

In some embodiments of the invention, ligands that bind the IL-13Rα2 receptor are peptides. In some embodiments, the agent is IL-13 or a fragment thereof or mutant thereof (inclusive of fragments of mutant IL-13) that specifically binds IL-13α2.

Recombinant IL-13 is commercially available from a number of sources (e.g., R&D Systems, Minneapolis, Minn., and Sanofi Bio-Industries, Inc., Tervose, Pa.). Alternatively, a gene or cDNA encoding IL-13 may be cloned into a plasmid or other expression vector and expressed in any of a number of expression systems according to methods well known to those of skill in the art. Methods of cloning and expressing IL-13 and the nucleic acid sequence for IL-13 are well known (see, e.g., Minty et al. (1993) and McKenzie (1987)). Specific IL-13 mutants are also known and described in U.S. Pat. No. 6,630,576 (Debinski) and U.S. Pat. No. 6,884,603 (Debinski et al.), which are incorporated by reference herein. In some embodiments, the IL-13 mutant is IL-13.EI3K, which has an amino acid residue at position 13 substituted for lysine. Other IL-13 mutants useful in the present invention include, but are not limited to, IL-13.R66D, IL-13.S69D, and IL-13.K105R. See Van Nguyen et al., Neuro-Oncology 14(10):1239-1253 (2012). Any mutant or combination of mutants may be used.

One of skill in the art will appreciate that analogues or fragments of IL-13 or IL-13 mutants will also specifically bind to IL-13Rα2. For example, conservative substitutions of residues (e.g., a serine for an alanine or an aspartic acid for a glutamic acid) comprising native IL-13 may provide IL-13 analogues that also specifically bind to the IL-13 receptor. Thus, the terms "IL-13" or "IL-13 mutant" when used in reference to a targeting molecule, also includes fragments, analogues or peptide mimetics of IL-13 or IL-13 mutants that also specifically bind to the IL-13 receptor. Further discussion of IL-13 as contemplated by the present invention can be found in U.S. Pat. No. 5,328,984 (Pastan et al.), U.S. Pat. No. 5,614,191 (Puri et al.), U.S. Pat. No. 5,919,456 (Puri et al.), U.S. Pat. No. 6,296,843 (Debinski), U.S. Pat. No. 6,428,788 (Debinski et al.), U.S. Pat. No. 6,518,061 (Puri et al.), 6,576,232 (Debinski et al.), U.S. Pat. No. 6,630,576 (Debinski), U.S. Pat. No. 6,884,603 (Debinski et al.) and U.S. Pat. No. 8,362,207 (Debinski et al.).

In some embodiments, the internalizing factor or targeting peptides of the present invention are not IL-13 or IL-13 mutants and/or fragments, but instead are peptides that do not bind to the IL-13 binding site, but instead bind to a different binding site on the IL-13 receptor. Further discussion of peptides as contemplated by the present invention can be found in U.S. Pat. No. 8,362,207 and U.S. 2013/0209541 (Debinski et al.).

These peptides include, but are not limited to, a peptide of FORMULA I (SEQ ID NO:7):

$$X-R^1-R^2-R^3-R^4-R^5-R^6-R-Y \qquad (I)$$

wherein:
$R^1$ is G or S;
$R^2$ is E or D;
$R^3$ is M, W, Y, or I;
$R^4$ is G, S or A;
$R^5$ is W, F, H or Y;
$R^6$ is V, P, T or N;
$R^7$ is R, K or H; and
X and Y can each independently be present or absent and when present can each independently be a capping group, a linking group, an amino acid optionally terminated by a capping group or linking group, or a peptide consisting of from 2 to 10 additional amino acids optionally terminated by a capping group or linking group.

In some embodiments, the peptide comprises: ACGEMG-WVRCGGGS (SEQ ID NO:8), CGEMGWVRC (SEQ ID NO:9) or GEMGWVR (SEQ ID NO:10).

The peptide may also have a structure of FORMULA II (SEQ ID NO: 11):

$$X-R^1-R^2-R^3-R^4-R^5-R^6-R^7-Y \qquad (II)$$

wherein:
$R^1$ is L, A, I, V, or M;
$R^2$ is P, V, T or N;
$R^3$ is Q, N, D, E or H
$R^4$ is L, A, I, V, or M;
$R^5$ is W, F, H or Y;
$R^6$ is L, A, I, V, or M;
$R^7$ is F, W, H or Y; and
X and Y an each independently be present or absent and when present can each independently be a capping group, a linking group, an amino acid optionally terminated by a capping group or linking group, or a peptide consisting of from 2 to 10 additional amino acids optionally terminated by a capping group or linking group.

In some embodiments, the peptide comprises: ACLPQL-WLFCGGGS (SEQ ID NO:12), CLPQLWLFC (SEQ ID NO:13), or LPQLWLFC (SEQ ID NO:14).

The peptide may also have a structure of FORMULA III (SEQ ID NO:15):

$$X-R^1-R^2-R^3-R^4-R^5-R^6-R-Y \qquad (III)$$

wherein:
R¹ is S or G;
R² is P, V, T or N;
R³ is F, W, H or Y;
R⁴ is L, A, I, V, or M;
R⁵ is H, W, F, or Y;
R⁶ is L, A, 1, V, or M;
R⁷ is L, A, I, V, or M; and
X and Y an each independently be present or absent and when present can each independently be a capping group, a linking group, an amino acid optionally terminated by a capping group or linking group, or a peptide consisting of from 2 to 10 additional amino acids optionally terminated by a capping group or linking group.

In some embodiments, the peptide comprises: ACSPFL-HLLCGGGS (SEQ ID NO:16), CSPFLHLLC (SEQ ID NO:17), or SPFLHLL (SEQ ID NO:18).

The targeting peptides of the present invention can be coupled to or conjugated to one or more effector molecules, cytosol localization elements, and/or subcellular compartment localization signal elements by any suitable technique, including those described further below. The described constructs can be used for therapeutic and/or diagnostic purposes.

D. CONSTRUCTS

In some embodiments, one, two, three or four ligands as taught herein are provided along with an effector molecule in a multi-valent conjugate construct. The conjugate in some embodiments includes a linker between ligands and/or between one or more ligands and one or more effector molecules, cytosol localization elements, and/or subcellular compartment localization signal elements. In some embodiments, the construct comprises one or more contiguous polypeptides, which may comprise one or more components as taught herein. In some embodiments, one or more polypeptides are conjugated to each other, e.g., through disulfide bonding or other chemical modification, to form the construct See, e.g., U.S. Pat. No. 8,664,407 to Chen et at.

As a non-limiting example, a first polypeptide may have the formula (e.g., N terminus to C terminus):
A-B-C-D-E,
E-D-C-B-A,
A-B-D-C-E, or
E-C-D-B-A,
wherein:
A is a ligand that binds to EphA2, EphA3 and/or EphB2;
B is a linker (which may or may not comprise a peptide);
C is a cytosol localization element;
D is present or absent and is a subcellular compartment localization signal element; and
E is an effector molecule (which may or may not comprise a peptide).

A second polypeptide construct may have the formula (e.g., N terminus to C terminus):
F-G-H, or
H-G-F
wherein:
F is a ligand that binds to EphA2, EphA3 and/or EphB2;
G is a linker (which may or may not comprise a peptide); and
H is a ligand that binds to IL-13Rα2.

In some embodiments, the first polypeptide construct is covalently bound to the second polypeptide construct (e.g., through disulfide bonding of peptide linkers) to form a multi-valent targeting construct as taught herein.

A further polypeptide construct may have the formula (e.g., N terminus to C terminus):
F-G-C-D-E,
E-D-C-O-F,
F-G-D-C-E, or
E-C-D-G-F
wherein:
F is a ligand that binds to EphA2, EphA3 and/or EphB2;
G is present or absent and is a linker (which may or may not comprise a peptide);
C is a cytosol localization element;
D is present or absent and is a subcellular compartment localization signal element; and
E is present or absent and is an effector molecule (which may or may not comprise a peptide).

As another non-limiting example, a first polypeptide may have the formula (e.g., N terminus to C terminus):
A-B-C-D-E,
E-D-C-B-A,
A-B-D-C-E, or
E-C-D-B-A,
wherein:
A is a ligand that binds to IL-13Rα2;
B is present or absent and is a linker (which may or may not comprise a peptide);
C is a cytosol localization element;
D is present or absent and is a subcellular compartment localization signal element; and
E is present or absent and is an effector molecule (which may or may not comprise a peptide).

A second polypeptide construct may have the formula (e.g., N terminus to C terminus):
F¹-G-F²,
wherein:
F¹ and F² are each independently a ligand that binds to EphA2, EphA3 and/or EphB2; and
G is a linker (which may or may not comprise a peptide).

Figure 7I:
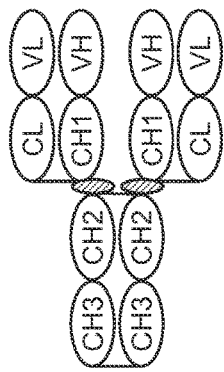
Figure 7I:
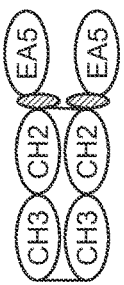
Figure 7I:
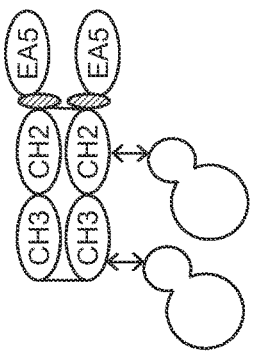
Figure 7I:
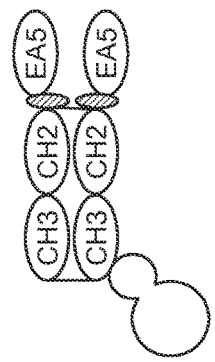
Figure 7I:
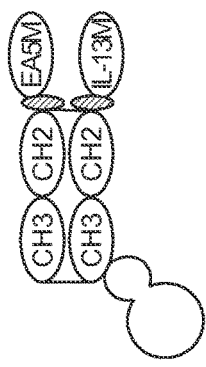
Figure 7I:
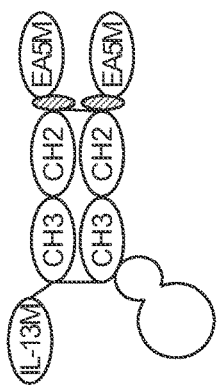
Figure 7I:
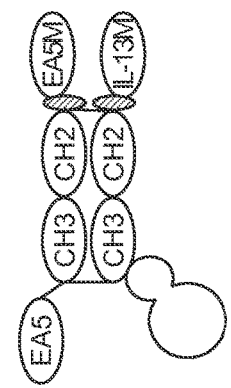
Figure 7I:
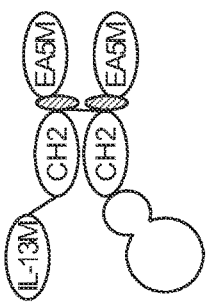
Figure 7I:
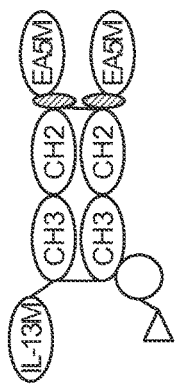
Figure 8A:
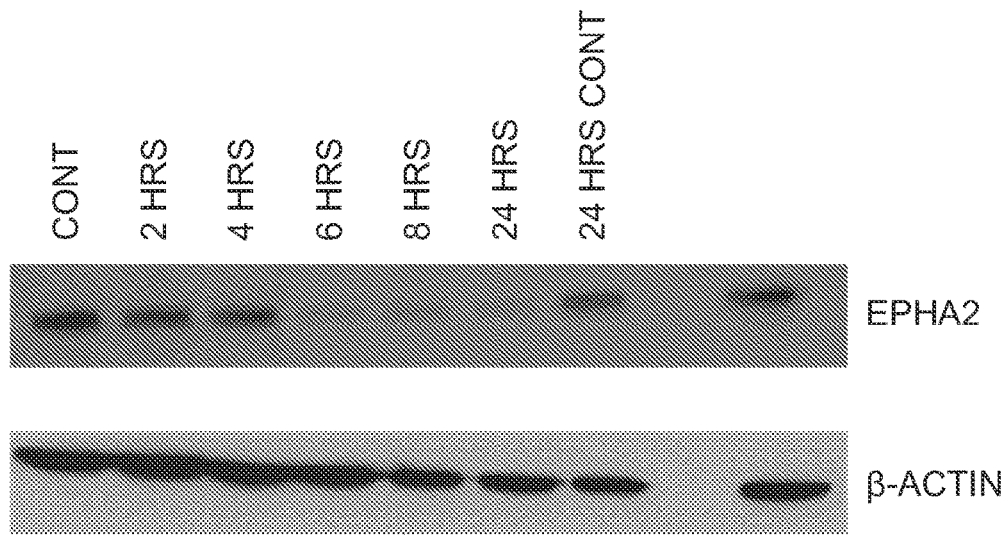
FIG. 8A-8B presents data demonstrating downregulation of EphA2 upon treatment with a bivalent construct. 8A: effect on EphA2 downregulation after treatment with the bivalent construct eA5-Fc-IL-13.E13K. 8B: effect on EphA2 downregulation after treatment with eA5-Fc-stop.
Figure 8B:
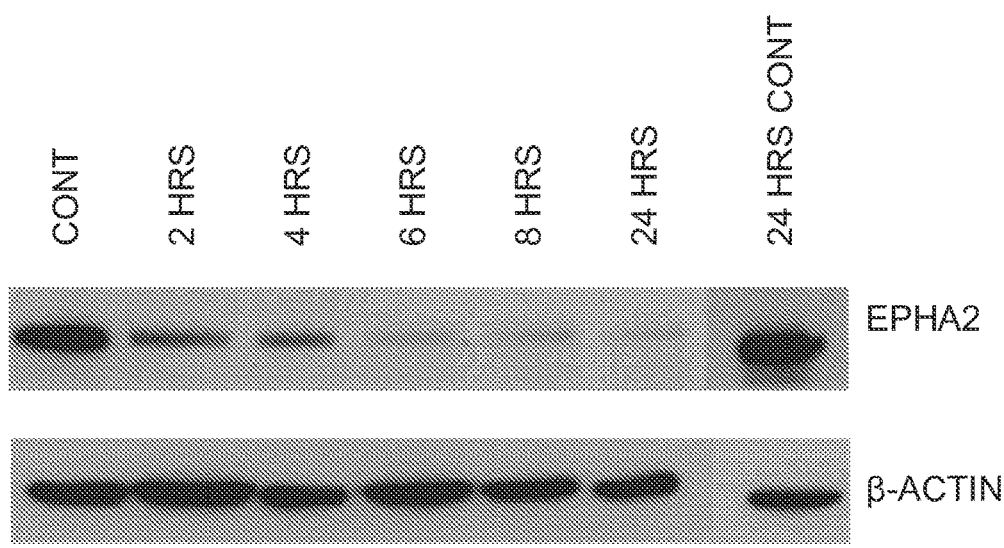
Figure 9A:
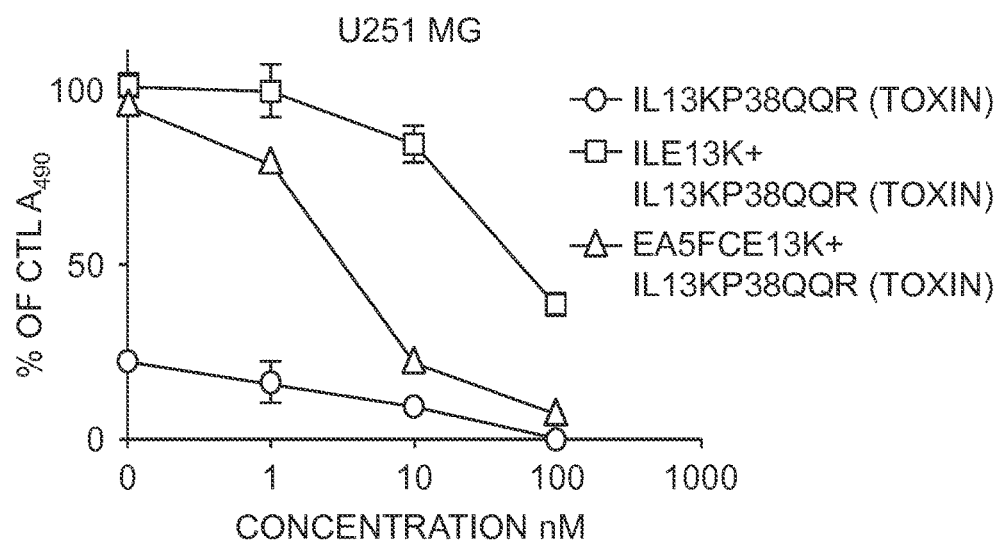
FIG. 9A-9B presents data demonstrating the neutralization of the action of an IL-13 based cytotoxin upon treatment with the bivalent construct eA5-Fc-IL-13.E13K.
Figure 9B:
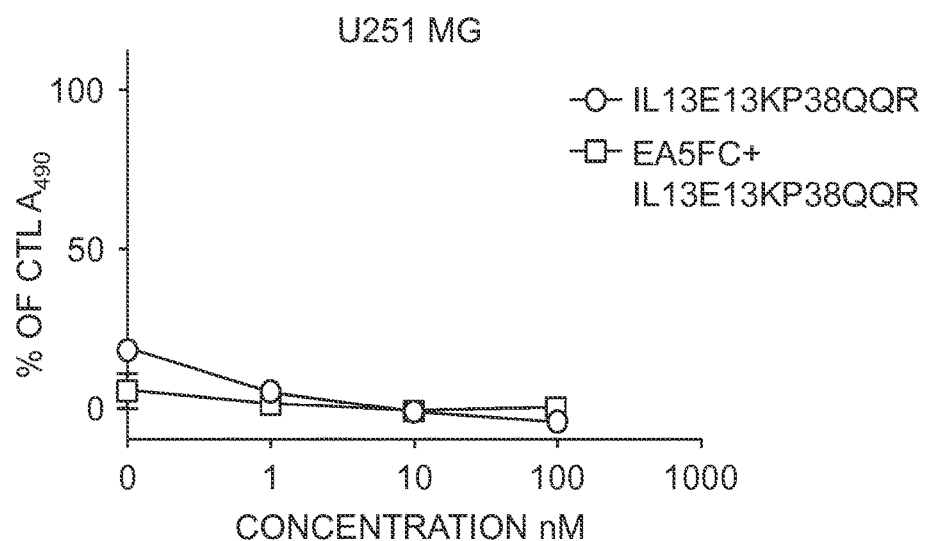

Again, in some embodiments, one polypeptide construct may be covalently bound to another polypeptide construct (e.g., through disulfide bonding) to form a multi-valent targeting construct as taught herein. Examples of these and other embodiments of the multi-valent targeting constructs are provided in FIG. 7.

Protein constructs may be produced using methods known in the art, e.g., bacterial expression, prokaryotic or eukaryotic expression, etc. See, e.g., U.S. Pat. No. 7,381,408 to Mezo et al.; U.S. Pat. No. 7,655,413 to Butt et al.; and U.S. Pat. No. 8,603,807 to Reed. In some embodiments, protein components may be produced by bacterial expression and/or by eukaryotic expression. For example, glycosylated eA5-Fc can be produced using a baculovirus expression system in insect cells, and PE38QQR can be produced in bacteria.

Ligands as described herein may be coupled to or conjugated to a linker, another ligand and/or an effector molecule such as a diagnostic and/or therapeutic agent in accordance with any of a variety of techniques, such as those employed in the production of immunoconjugates. See, e.g., U.S. Pat. No. 6,949,245 to Sliwkowski.

In some embodiments, the conjugate is internalized in response to carrier/ligand binding. For example, EphA2 is over-expressed in a majority of patients with GBM and its ligand induces a receptor-mediated internalization once it binds the receptor (Walker-Daniels et al. (2002) Mol. Cancer Res. 1:79-87). The latter may be used for, e.g., recombinant bacterial toxin-containing cytotoxins to exert anti-tumor action (Debinski (2002) Molecular "Targeting of Brain Tumors with Cytotoxin," In: Chimeric Toxins (Lorberboum-Galski & Lazarovici, eds., Harwood Academic Publishers) pp. 222-246; Debinski (2002) Cancer Invest. 20:801-809; Debinski (2002) Cancer Invest. 20:801-809). In addition, the IL-13Rα2 receptor ligand is internalized through receptor mediated endocytosis. See also U.S. Pat. No. 8,362,207 to Debinski et al.

Chemotherapeutic agents useful as effectors include those described above. Small molecule toxins, such as a calicheamicin, a maytansine (See U.S. Pat. No. 5,208,020), a trichothene, and CC 1065 are also contemplated herein as effectors. In some embodiments, *Pseudomonas* exotoxins are used as effectors (U.S. Pat. No. 5,328,984 to Pastan et al.).

Enzymatically active toxins and fragments thereof which can be used as effectors include *diphtheria* A chain, non-binding active fragments of *diphtheria* toxin, exotoxin A chain (from *Pseudomonas aeruginosa*), ricin A chain, abrin A chain (from *Corrybacterium typhimuriae*), modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, WO 93/21232.

Effectors may also include a compound with nucleolytic activity (e.g., a ribonuclease or a DNA endonuclease such as a deoxyribonuclease; DNase).

A variety of radioactive isotopes or radionuclides are available for the production of radioconjugated constructs as described above.

The linker may or may not be a peptide. Non-peptide linkers may include aliphatic hydrocarbon linkers such as an alkyl, alkenyl or alkynyl, optionally including one or more functional groups suitable for covalent attachment of ligands, localization elements and/or effectors.

In some embodiments, conjugates of a targeting ligand, linker and/or therapeutic agents or detectable groups may be made using a variety of bi-functional protein coupling agents such as N-succinimidyl-3-(2-pyridyldithiol)propionate (SPDP), succinimidyl-4-(N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin conjugate can be prepared as described in Vitetta et al. (1987) Science 238: 1098. Carbon-14-labeled 1-isothiocyanatobenzyl-3-methyl-diethylene triaminepentaacetic acid (MX-DTPA) is an exemplary chelating agent for conjugation of radionucleotide to the targeting peptide. See WO 94/11026. The linker may be a "cleavable linker" facilitating release of the cytotoxic drug in the cell. For example, an acid-labile linker, peptidase-sensitive linker, dimethyl linker or disulfide-containing linker (Chari et al. (1992) Cancer Res. 52:127-131) may be used.

In some embodiments, the linker may comprise an Fc domain or fragment thereof that is attached, directly or indirectly (for example, through a chemical spacer), to a ligand, localization element and/or effector molecule. The terms, "Fc", "Fc domain" or "Fc fragment," encompass native and altered forms of polypeptides derived from the Fc region of an antibody that are bound by an Fc receptor. In some embodiments, the Fc domain is derived from a human antibody (I.e., "human" Fc). The Fc domain normally has at least two heavy chain constant region domains (CH2 and CH3).

Forms of such Fc domains containing the hinge region that promotes dimerization are also included. One suitable Fc fragment, described in PCT applications WO 2005/047334 A1 and in WO 2004/074455 A2, is a single chain polypeptide extending from the N-terminal hinge region to the native C-terminus.

Also contemplated are altered forms of Fc fragments, for example, having improved serum half-life, altered effector functions, altered spatial orientation, and the like. The alteration of the Fc fragment can be achieved using any genetic engineering techniques known in the art. In some embodiments, the Fc domain is linked to more than one, for example, two, three or four, effector molecules.

Conjugation of the Fc domain may be performed using methods known in the art. See, e.g., U.S. 2010/0209424 to Roopenian et al. and U.S. 2012/0039880 to Yan et al., which are incorporated by reference herein. For example, a fusion protein including the ligand, localization signal element and/or effector may be made by recombinant techniques or peptide synthesis, which may also subsequently include covalent coupling of polypeptides, linkers and/or non-peptide effector(s).

In some embodiments, the Fc domain of the Fc fusion protein is a human Fc domain. The Fc domain may be from immunoglobulin G (IgG), IgA, IgE or IgM. In one embodiment, the Fc domain is from IgG, and may be from any of the subclasses of IgG. For example, in humans, there are four subclasses of IgG: IgG1; IgG2; IgG3; and IgG4. In some embodiments, the Fe domain is from human IgG1.

The Fc receptor to which binds the Fc domain of an Fc fusion protein of the invention is not particularly limited. For example, an Fc domain derived from IgG may bind to an Fc-gamma receptor (FcγR) and any members of the FcγR family. Examples of FcγR receptors include, but are not limited to, FcγRI, FcγRIIA, FcγRIIB, FcγRIIIA, FcγRIIIB and the neonatal Fc receptor (FcRn). Other receptors that may bind Fc fusion proteins of the invention include vascular endothelial growth factor (VEGF), tumor necrosis factor receptor (TNFR), receptor activator nuclear factor kappa b (RANK), and Tie-1 and Tie-2 receptors.

In some embodiments, the Fc domain may include an antibody-dependent cellular cytotoxicity (ADCC) activating domain and/or a complement-dependent cytotoxicity (CDC) activating domain. Such domains may be useful in engaging and/or activating immune cells to attack the targeted cancer cells and add to their cytotoxic potency. See, e.g., Di Gaetano et al., Complement Activation Determines the Therapeutic Activity of Rituximab In Vivo, J Immunol 171: 1581-87, 2003; U.S. Pat. No. 7,829,084 to Ledbetter et al.

In some embodiments, the effector molecule may be a *Pseudomonas* exotoxin or *Diphtheria* toxin. (U.S. Pat. No. 5,328,984 to Pastan et al. and U.S. Pat. No. 6,296,843 to Debinski). *Pseudomonas* exotoxins include, but are not limited to, *Pseudomonas* exotoxin A (PE). The *Pseudomonas* exotoxin can be modified such that it substantially lacks domain Ia, and *Pseudomonas* exotoxins may further include PE38QQR and PE4E. *Diphtheria* toxins include DT390, a *diphtheria* toxin in which the native binding domain is eliminated.

It will be appreciated that the ligands and/or effector molecules can be connected to either of the amino terminus, or the carboxyl terminus, of a polypeptide linker, in addition to an internal amino acid (such as a cysteine).

The present invention further contemplates a fusion protein comprising, consisting of, or consisting essentially of the targeting protein and a cytosol localization element, which can be made by, for example, recombinant techniques or peptide synthesis. In some embodiments, this fusion protein also comprises at least one effector molecule.

"Cytosol localization element" (also referred to as an endosomal exit element) as used herein refers to an amino acid sequence used to direct a target protein, fusion protein, or fragment thereof to the cytoplasm. The amino acid sequence can be of any size and composition, for example 3 to 100 amino acids in length to, 4, 5, 6, 7, 8, 10, 12, 15, 20, 25, 30, 40, 50, 60, 70, 80, 90 or 100 amino acids in length. In some embodiments, the cytosol localization element enables the fusion protein or a fragment thereof to exit an endocytic compartment after being internalized in the process of receptor-mediated internalization and enter the cytoplasm. In some embodiments the cytosol localization element is proteolytically activated, such as, but not limited to, by a calcium-dependent serine endoprotease, such as furin. Exemplary cytosol localization elements include, but are not limited to cytosol localization elements of bacterial toxins. Such bacterial toxins include, but are not limited to *Pseudomonas* exotoxin A (PE) (particularly domain II), *Diphtheria* toxin (DT), and Ricin A chain. Additional examples are described in: B. Beaumelle et al., Selective translocation of the A chain of *Diphtheria* toxin across the membrane of purified endosomes. *J. Biol. Chem.* 267: 11525-11531 (1992); I. Madshus et al., Membrane translocation of *Diphtheria* toxin carrying passenger protein domain, *Inf Immun.* 60:3296-3302 (1992); H. Stenmark et al., Peptides fused to the amino-terminal end of *Diphtheria* toxin are translocated to the cytosol, *J. Cell Biol.* 113:1025-1032 (1991); and R. Chignola et al., Self-potentiation of ligand-toxin conjugates containing Ricin A chain fused with viral structures, *J Biol Chem* 270:23345-23351 (1995). Still other exemplary cytosol localization elements include those describe in U.S. Pat. No. 6,235,526, which is incorporated herein by reference.

The present invention further contemplates a fusion protein comprising, consisting of, or consisting essentially of a targeting protein, linker and a subcellular compartment localization signal element, which can be made by, for example, recombinant techniques or peptide synthesis. In some embodiments this fusion protein also comprises, consists of, or consists essentially of a cytosol localization element and optionally an effector molecule.

"Subcellular compartment localization signal element" as used herein refers to a signal sequence or tag used to direct a target protein, fusion protein, or fragment thereof to particular cellular organelles. In some embodiments, the subcellular compartment localization signal element comprises a peptide sequence. Such peptide sequences can be of any size and composition, for example 3 to 100 amino acids in length, or 4, 5, 6, 7, 8, 10, 12, 15, 20, 25, 30, 40, 50, 60, 70, 80, 90 or 100 amino acids in length. Exemplary cellular organelles include, but are not limited to, the nucleus, endoplasmic reticulum, Golgi apparatus, endosomes, lysosomes, peroxisomes and mitochondria. Various subcellular compartment localization signal elements are known and/or commercially available. Exemplary subcellular compartment localization signal elements include, but are not limited to, nuclear localization signals and lysosomal localization signals. Other exemplary subcellular compartment localization signal elements include those described in U.S. Pat. No. 7,585,636, which is incorporated herein by reference.

"Nuclear localization signals" as used herein refers to an amino acid sequence which directs a target protein, fusion protein, or fragment thereof into the nucleus of a cell. Generally, nuclear localization signals (NLS) are a class of short amino acid sequences which may be exploited for cellular import of linked or coupled cargo into the nucleus. Such amino acid sequences can be from 3 to 100 amino acids in length or 3 to 50, 4 to 30, or 4 to 20 amino acids in length. The nuclear localization sequences of the present invention can be: (i) a monopartite nuclear localization sequence exemplified by the SV40 large T antigen NLS (PKKKRKV, SEQ ID NO:19); (ii) a bipartite motif consisting of two basic domains separated by a variable number of spacer amino acids and exemplified by the *Xenopus nucleoplasmin* NLS (KRXXXXXXXXXXKKKL, SEQ ID NO:20); or (iii) noncanonical sequences such as M9 of the hnRNP A1 protein, the influenza virus nucleoprotein NLS, and the yeast Gal4 protein NLS (Dingwall and Laskey, Trends Biochem Sci 16:478-481, 1991). In some embodiments, the nuclear localization signal is a highly cationic or basic peptide. In some embodiments, the NLS comprises two or more Arg or Lys amino acid residues. In some embodiments, the NLS sequence binds to cytosolic proteins, such as importins and karyopherins, which recognize and transport NLS-containing proteins or peptides to the nuclear pore complex. The present invention envisions the use of any nuclear localization signal peptide, including but not limited to, SV40 virus T-antigen NLS and NLS sequences domain derived from viral Tat proteins, such as HIV Tat. Other exemplary nuclear localization signals include, but are not limited to, those discussed in Cokol et al., 2000, EMBO Reports, 1(5):411-415, Boulikas, T., 1993, Crit. Rev. Eukaryot. Gene Expr., 3:193-227, Collas, P. et al., 1996, Transgenic Research, 5: 451-458, Collas and Alestrom, 1997, Biochem. Cell Biol. 75: 633-640, Collas and Alestrom, 1998, Transgenic Research, 7: 303-309, Collas and Alestrom, 1996, Mol. Reprod. Devel., 45:431-438, and U.S. Pat. Nos. 7,531,624, 7,498,177, 7,332,586, and 7,550, 650, all of which are incorporated by reference.

"Lysosomal localization signal" as used herein refers to an amino acid sequence which directs a target protein or fusion protein to lysozymes. Examples include, but are not limited to, lysosome associated membrane protein 1 (LAMP-1) tail sequence: RKRSHAGYQTI (SEQ ID NO:21), lysosomal acid phosphatase (LAP): RLKRMQAQPPGYRHVADGEDHAV (SEQ ID NO:22), and lysosomal integral membrane protein 2 (LIMP-2): RGQGSTDEGTADERAPLIRT (SEQ ID NO:23).

In further embodiments of the present invention the fusion protein comprises, consists of, or consists essentially of a targeting protein comprising eA5, a mutant of eA5 or an analogue or fragment thereof; a linker; a cytosol localization element comprising a *Pseudomonas* exotoxin A (PE) or *Diphtheria* toxin (DT); optionally a subcellular compartment localization signal element comprising a nuclear localization signal or a lysosomal localization signal, optionally further comprising a radiopharmaceutical or chemotherapeutic.

E. PHARMACEUTICAL FORMULATIONS AND METHODS

The active constructs, conjugates, and/or compositions thereof described herein may be formulated for administration in a pharmaceutical carrier in accordance with known techniques. See, e.g., Remington, *The Science and Practice of Pharmacy* (9th Ed. 1995). In the manufacture of a pharmaceutical formulation according to the invention, the active construct(s) (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the construct(s) as a unit-dose formulation, for example, a tablet, which may contain from 0.01 or 0.5% to 95% or 99% by weight of the active construct. One or more active constructs may be incorporated in the formulations of the invention, which may be prepared by any of the well-known techniques of pharmacy comprising admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active construct which is being used.

Particular routes of parenteral administration include intrathecal injection (also for brain tumors spread locally to meninges), including directly into the tumor or a tumor resection cavity, and intraventricular injection into a ventricle of the brain.

Active constructs and compositions may be administered by intratumor injection (including tumors in any region such as tumors of the brain).

Formulations of the present invention suitable for parenteral administration comprise sterile aqueous and non-aqueous injection solutions of the active construct, which preparations are preferably isotonic with the blood of the intended recipient. These preparations may contain anti-oxidants, buffers, bacteriostats and solutes that render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising an active construct or composition in a unit dosage form in a sealed container. The construct or composition is provided in the form of a lyophilizate that is capable of being reconstituted with a suitable pharmaceutically acceptable carrier to form a liquid composition suitable for injection thereof into a subject. The unit dosage form typically comprises from about 10 mg to about 10 grams of the construct or composition. When the construct or composition is substantially water-insoluble, a sufficient amount of emulsifying agent that is physiologically acceptable may be employed in sufficient quantity to emulsify the construct or composition in an aqueous carrier. One such useful emulsifying agent is phosphatidyl choline.

Further, the present invention provides liposomal formulations of the constructs disclosed herein and compositions thereof. The technology for forming liposomal suspensions is well known in the art. When the construct or composition thereof is an aqueous-soluble composition, using conventional liposome technology, the same may be incorporated into lipid vesicles. In such an instance, due to the water solubility of the construct or composition, the construct or composition will be substantially entrained within the hydrophilic center or core of the liposomes. The lipid layer employed may be of any conventional composition and may either contain cholesterol or may be cholesterol-free. When the construct or composition of interest is water-insoluble, again employing conventional liposome formation technology, the composition may be substantially entrained within the hydrophobic lipid bilayer that forms the structure of the liposome. In either instance, the liposomes that are produced may be reduced in size, as through the use of standard sonication and homogenization techniques.

Liposomal formulations containing the constructs disclosed herein or compositions thereof (e.g., multi-valent conjugates), may be lyophilized to produce a lyophilizate, which may be reconstituted with a pharmaceutically acceptable carrier, such as water, to regenerate a liposomal suspension. Examples of liposomal formulations that can be used include the neutral lipid 1,2-dioleoyl-sn-glycero-3-phosphatidylcholine (DPOC) (See, e.g., Landen Jr. et al. (2005) Cancer Res. 65:6910-6918).

Other pharmaceutical compositions may be prepared from the water-insoluble constructs disclosed herein, or compositions thereof, such as aqueous base emulsions. In such an instance, the composition will contain a sufficient amount of pharmaceutically acceptable emulsifying agent to emulsify the desired amount of the construct or composition thereof. Particularly useful emulsifying agents include phosphatidyl cholines, and lecithin.

In addition to active constructs, the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well-known in the art.

The therapeutically effective dosage of any one active agent, the use of which is in the scope of present invention, will vary somewhat from construct to construct, and patient to patient, and will depend upon factors such as the age and condition of the patient and the route of delivery. Such dosages can be determined in accordance with routine pharmacological procedures known to those skilled in the art.

As a general proposition, the initial pharmaceutically effective amount of the active construct administered parenterally will be in the range of about 0.1 to 50 mg/kg of patient body weight per day, with the typical initial range used being 0.3 to 20 mg/kg/day, more preferably 0.3 to 15 mg/kg/day. The desired dosage can be delivered by a single bolus administration, by multiple bolus administrations, or by continuous infusion administration of active construct, depending on the pattern of pharmacokinetic decay that the practitioner wishes to achieve.

The active construct(s) may be suitably administered to the patient at one time or over a series of treatments. Depending on the type and severity of the disease, about 1 µg/kg to 15 mg/kg (e.g. 0.1-20 mg/kg) of active construct(s) is an initial candidate dosage for administration to the patient, whether, for example, by one or more separate administrations, or by continuous infusion. A typical daily dosage might range from about 0.1, 0.5, 1, 10 or 100 µg/kg up to 100, 200 or 500 mg/kg, or more, depending on the factors mentioned above. For repeated administrations over several days or longer, depending on the condition, the treatment is sustained until a desired suppression of disease symptoms occurs. A more particular dosage of the active construct will be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g., such that the patient receives from about two to about twenty, e.g. about six doses of the anti-ErbB2 antibody). An initial higher loading dose, followed by one or more lower doses may be administered. An exemplary dosing regimen comprises administering an initial loading dose of about 0.5 to 10 mg/kg, followed by a weekly maintenance dose of about 0.5 to 10 mg/kg of the active construct. However, other dosage regimens may be useful. The progress of this therapy is easily monitored by conventional techniques and assays.

Subjects treated by the methods of the present invention can also be administered one or more additional therapeutic agents. See U.S. Pat. No. 5,677,178. Chemotherapeutic agents may be administered by methods well known to the skilled practitioner, including systemically, direct injection into the cancer, or by localization at the site of the cancer by associating the desired chemotherapeutic agent with an appropriate slow release material or intra-arterial perfusing of the tumor. The preferred dose may be chosen by the practitioner based on the nature of the cancer to be treated, and other factors routinely considered in administering. See, e.g., U.S. Pat. No. 7,078,030.

In some embodiments, the active agent or construct is administered directly into the brain (i.e., within the blood brain barrier) and/or other portions of the central nervous system of a subject. In some embodiments, the active agent is administered to the subject intra-cerebrally. In some embodiments, the active agent is administered to the subject by intracerebroventricular infusion. In some embodiments, the active agent is administered by intrathecal delivery. In some embodiments, the active agent is administered by convection-enhanced delivery.

Convection-enhanced delivery (CED) is the continuous injection under positive pressure of a fluid containing a therapeutic agent. In the central nervous system (CNS), this delivery technique circumvents the blood-brain barrier in delivering agents. See, e.g., U.S. 2005/0002918 to Strauss et al.; U.S. 2012/0041394 to Haider et al.; U.S. 2012/0209110 to Bankiewicz et al. CED uses a fluid pressure gradient established at the tip of an infusion catheter and bulk flow to propagate substances within the extracellular fluid space. CED allows the extracellularly-infused material to further propagate via the perivascular spaces and the rhythmic contractions of blood vessels acting as an efficient motive force for the infusate. As a result, a higher concentration of drug can be distributed more evenly over a larger area of targeted tissue than would be seen with a simple injection. CED has been clinically tested in the fields of neurodegenerative diseases and neurooncology, and is useful in a broad field of applications, such as the delivery of small molecules, macromolecules, viral particles, magnetic nanoparticles, and liposomes.

In some embodiments, the construct is administered in combination with radiation therapy. In some embodiments, the construct is administered in combination with surgery to remove at least some of the cancerous tissue. In some embodiments, the construct is administered in combination with another, different chemotherapy agent.

Radiation therapy may include, e.g., external beam radiotherapy, which may be at any suitable dose (e.g., 20 to 70 Gy or more per tumor, typically delivered over a fractionated schedule).

Pharmaceutical compositions containing a targeting construct without an effector may be administered to subjects as blocking reagents, in like manner as described in Abrams et al., U.S. Patent No. RE38,008, in conjunction with the administration of a targeting construct coupled to an effector such as a therapeutic group.

The targeting construct coupled to a detectible group may also be used in vitro as histological reagents on tissue samples, where binding of, e.g., the EphA3 receptor is indicative of cancer tissue in the tissue sample.

The present invention is further described in the following non-limiting examples.

EXAMPLES

Example 1

EphA2 and EphA3 Localize to Different GBM Tumor Compartments

An eA5-based cytotoxin was generated to target both EphA2 and EphA3. Here it is shown for the first time that EphA3 and EphA2 localized in different areas of the tumor and they can be simultaneously targeted by a novel eA5-based cytotoxin that is internalized and potently kills receptor expressing cells with an IC50~10-11 mol/L. The strategy of using a single therapeutic to hit multiple sub-population of receptors-overexpressing tumor cells allows targeting of different tumor compartments and offers an advantage in the prospective combinatorial therapy.

Cell Lines.

GBM cell lines U-251 MG, U-373 MG and T98G were obtained from the American Type Culture Collection (ATCC, Manassas, Va.) and grown in the ATCC recommended media. G48a and the BTCOE human explants cells were grown in RPMI medium with 10% (v/v) FBS and glucose adjusted to 4 g/L. Sf9 insect cells were cultured in BD BaculoGold TNM-FH insect serum media (BD) and in BD BaculoGold Max-XP serum-free insect cell media (BD) with the addition of 2% L-Glutammine and Gentamicin (10 µg/mL). Western Blots. Cell lysates were prepared and separated by SDS-PAGE. Western blotting was performed as previously described (2-6). Primary antibodies were used at the following concentrations: rabbit polyclonal EphA3 (1:1000, Santa Cruz Biotechnology), mouse monoclonal EphA2 (1:1000, Millipore) and β-actin (1:50,000, Sigma) rabbit polyclonal eA1 (1:500, Santa Cruz Biotechnology), mouse monoclonal eA5 (1:500, Santa Cruz Biotechnology).

Recombinant Protein Expression and Chemical Conjugation.

EA5 gene was synthesized (GenScript, Piscataway, N.J.) based on the GeneBank database (NCBI) sequence AAH75054.1. The gene was amplified by PCR using the forward primer: 5'-TAAGGATCCCAGGACCCG-3' (SEQ ID NO:24) and the reverse primer: 5'-GTACAATTGCGGT-GTCATCT-3' (SEQ ID NO:25), cloned into BamHI-EcoRI sites in the modified Baculovirus transfer vector pAcGP67-B (BD Biosciences) and sequenced (Genewiz, Research Triangle Park, N.C.). Recombinant eA5 (aa. 21-191) was produced in the dimeric form (C-terminal Fc tag) in the Baculovirus expression system (BD Biosciences, San Diego, Calif.). Sf9 insect cells were co-transfected and protein collected and purified as previously described (2-6). PE38QQR was produced in BL21 bacteria cells and purified as previously described (4). Conjugation of eA5-Fc and PE38QQR was done using the Protein-Protein Cross-linking Kit (Molecular Probes) in a 1:3 molar ratio eA5-Fc:PE38QQR following the instruction of the supplier and as previously described (4).

Cell Viability Assay.

Cells were plated in 96-well tissue culture plates at different concentrations (U-251 MG and U373 MG: 103 cells/well; G48a, T98G, BTCOE4536 and BTCOE4795: 2.5×103 cells/well) and allowed to adhere and proliferate for 24 h. EA5 cytotoxin was diluted in 1% PBS/BSA. For receptor blocking eA1-Fc or eA5-Fc (10 µg/mL) was added 1 h before the cytotoxin. Cells were treated with cycloexamide as positive control for cell death. Cells were incubated for 48 or 72 h at 37 C. Cell viability was determined by the MTS (3-(4,5-dimethylthiazol-2-yl)-5-(3-carboxymethoxyphenyl)-2-(4-sulfophenyl)-2H-tetrazolium, inner salt)/phenazine methosulfate cell proliferation assay (Promega) as recommended by the supplier.

Immunofluorescent Staining.

Cells were grown overnight on sterile glass slides in the appropriate media. Slides were washed twice in phosphate-buffered saline (PBS) and fixed for 2 min in acetone at −20 C. Slides were washed twice in PBS and blocked for 1 h in 5% PBS/bovine serum albumin (BSA) at room temperature. EphA3 (1:250, Santa Cruz), EphA2 (1:100, Millipore), NeuN (1:300, Millipore), GFAP (1:250, Santa Cruz) and CD31 (1:300, Pierce) primary antibodies were diluted in 1% PBS/BSA and incubated overnight at 4 C. Slides were washed twice in PBS, 5 min each, and incubated with secondary antibodies (1:200, AlexaFluor, Lifetech) and Nuclear Counterstain (DAPI, 1:1000) in 1% PBS/BSA for 1 h at room temperature. Slides were washed two times for 5 min each in PBS and mounted with fluoroguard.

U251-MG Time Course and Downregulation Assay.

1.5×105 U-251 MG cells were plated in 60 mm dishes and grown over-night at 37 C, 5% CO2. The next day, cells were treated with different 1 µg/mL concentration of recombinant eA5-Fc. Treated cells were incubated for the indicated time before lysing the cells to check EphA2 and EphA3 degradation. Cell lysates were prepared as previously described (2).

These studies demonstrate that EphA3 is over-expressed in GBM tumor specimens when compared to normal brain and is often localized on the invasive edge of the tumor. Thus, EphA3 is a potential target for GBM tumor initiating cells.

EphA3 and EphA2, both membrane receptors overexpressed in GBM, localized on different compartments within the tumor area and are only partially co-localized.

Finally, it is demonstrated that EphA3 and EphA2 can be both specifically targeted with eA5-PE38 cytotoxin, which potently kills GBM tumor cells with an IC50~10-11 mol/L.

REFERENCES CITED IN EXAMPLE 1

1. Beauchamp A, Debinski W. (2012) Ephs and Ephrins in Cancer: Ephrin-A1 Signaling. Semin Cell Dev Biol. 23: 109-115
2. Ferluga S, Hantgan R, Goldgur Y, Himanen J P, Nikolov D B, Debinski W. (2012) Biological and structural characterization of glycosylation on ephrin-A1, a preferred ligand for EphA2 receptor tyrosine kinase. J Biol Chem; 288: 18448-57
3. Wykosky J, Gibo D M, Stanton C, Debinski W. (2005) EphA2 as a novel molecular marker and target in glioblastoma multiforme. Mol Cancer Res; 3: 541-551
4. Wykosky J, Gibo D M, Debinski W. (2007) A novel, potent, and specific ephrinA1-based cytotoxin against EphA2 receptor expressing tumor cells. Mol Cancer Ther; 6: 3208-3218
5. Wykosky J, Palma E, Gibo D M, Ringler S, Turner C P, Debinski W. (2008) Soluble monomeric EphrinA1 is released from tumor cells and is a functional ligand for the EphA2 receptor. Oncogene; 27: 7260-7273
6. Lema Tome C M, Palma E, Ferluga S, Lowther W T, Hantgan R, Wykosky J, Debinski W. (2012) Structural and functional characterization of the monomeric EphrinA1 binding site to the EphA2 receptor. J Biol Chem; 287:14012-22
7. Day B W, Stringer B W, Al-Ejeh F, Ting M J, Wilson J, Ensbey K S, Jamieson P R, Bruce Z C, Lim Y C, Offenhäuser C, Chanmsaz S, Cooper L T, Ellacott J K, Harding A, Leveque L, Inglis P, Allan S, Walker D G, Lackmann M, Osborne G, Khanna K K, Reynolds B A, Lickliter J D, Boyd A W. (2013) EphA3 maintains tumorigenicity and is a therapeutic target in glioblastoma multiforme. Cancer Cell; 23: 238-428

Example 2

Simultaneous Targeting of Eph Receptors with an eA5-Based Cytotoxin

EphA2, a protein tyrosine kinase receptor, is a therapeutic target in glioblastoma (GBM) and an important factor in GBM ethiopathogenesis. EphA2 is over-expressed in ~60% of GBM, but not in normal brain. In an effort to find additional targets in GBM, it was found that the Eph receptor A3 was highly overexpressed under tumorsphere-promoting culture conditions of GBM cells.

The presence of EphA3 in GBM was examined in more detail. EphA3 was found to be overexpressed in 7 out of 12 specimens (58%) of the GBM tumor lysates tested, but not in normal brain, as well as in 5 out of 7 anaplastic oligodendrogliomas (71%), and less (~20-30%) in lower grade astrocytomas and meningiomas. EphA3 was also overexpressed in 6 out of 11 GBM established cell lines tested (55%) but not in SVG p12 glial cells.

Immunofluorescence staining on frozen sections of human GBM specimens localized EphA3 in scattered areas of the tumor, in the invasive ring, and in niches closed to tumor vessels, but not on the endothelium or on mature neurons. Importantly, EphA3 co-localized with microglia/macrophage markers.

An eA5-based cytotoxin with eA5-Fc and *Pseudomonas* exotoxin A was generated to target both Eph receptors A2 and A3. The cytotoxin potently killed GBM cells with an $IC_{50}$ approaching 10-11 M. This is the first example of simultaneous targeting of multiple receptors overexpressed in GBM and on a different subpopulation of cells using a single agent.

EphrinA5 (eA5) was utilized as a ligand binding domain in the production of a chimeric cytotoxin, taking advantage of its ability to bind both EphA2 and EphA3 with high affinity as well as EphB2. The data demonstrate success in simultaneously and specifically targeting these receptors overexpressed in GBM, but not in normal brain, that localize to different tumor compartments, therefore potently killing not only tumor cells but also that of the tumor microenvironment.

G48a cells were grown under tumorsphere-forming conditions. Microarray data analysis revealed that one of the most up-regulated genes was EphA3. The protein levels of EphA3 also increased approximately 3-4 times compared to usual in-adherence growing conditions. A high degree of co-localization of EphA3 was observed with the glioma cancer stem cell marker Nestin by immunofluorescent staining. These results suggest a possible role for EphA3 in tumor-initiating cell population.

Specimens of several tumors were analyzed for the presence of EphA3. The receptor was prominently overexpressed in 7 out of 12 of GBM tumor lysates (58%) but not in normal brain. In specimens that highly expressed EphA3, the eA5 ligand was usually poorly detectable. Only one specimen showed high levels of both ligand and receptor (BTCOE 4443). The same was observed for EphA2 and its corresponding ligand eA1, consistent with previous reports. EphA3 was also present in 5 out of 7 anaplastic oligodendrogliomas (WHO grade II/III) (71%), and less (~20-30%) in lower grade astrocytomas (WHO grade II) and meningiomas.

The presence of EphA3 was also examined by immunofluorescence staining on a human brain from a fast autopsy of a patient with GBM (G204). EphA3 was largely present in scattered areas within the tumor and of the invading ring, but not on the contralateral side. To analyze any possible presence of EphA3 on neuronal cells, sections were stained with NeuN antibody. No co-localization of EphA3 with neurons was observed in the tumor core and invading area, nor in the contralateral side of the diseased brain.

EphA3 and EphA2 localization was also analyzed by immunofluorescent staining of another frozen human GBM specimen. EphA3 was not detected on the vasculature, but it showed some degree of co-localization with EphA2 within the tumor area. EphA2 was found to be on tumor vasculature and in the surrounding areas.

EphA3 and EphA2 as well as that of eA5 and eA1 protein levels were studied by western blot on several established GBM cell lines. The receptors displayed similar, but not identical immunoreactive profile and were highly overexpressed in most of the cell lines tested compared to SVGp12 normal glial cells. The Eph receptor ligands, eA5 and eA1, were absent or barely detectable.

EphA3 and EphA2 cellular localization was also analyzed by immunofluorescent staining of U-251 MG, G48a and T98G GBM cell lines. The first two were chosen for having high levels of both receptors while T98G cells for displaying no detectable levels of either EphA3 or EphA2 by western blot analysis at the same short time exposure. EphA3 receptors displayed mainly a cytoplasmic staining, whereas the immunostained EphA2 was present on cell membranes and in the cytoplasm of the three cell lines analyzed.

EphA3 was further analyzed by flow cytometry on U-251 MG and T98G cells and compared to the IgG control. The results confirmed that EphA3 was, indeed, on the cell membrane in both cell lines.

EphA3 and EphA2 protein levels were also evaluated on early passage GBM cell lines and compared to that in tumors they are derived from. In all samples analyzed, EphA2 was highly over-expressed in the tumor-derived cell line compared to the originating tumor. The same was observed for EphA3 with the exception of only one sample (BT-COE4843) that showed the opposite trend.

Expression and localization of EphA3 was further analyzed on consecutive GBM frozen sections. EphA3 did not co-localize with the endothelial cell marker CD31, confirming that EphA3 was not present on the vasculature. EphA3 also showed a limited co-localization with the glial fibrillary acidic protein (GFAP).

Microglia/macrophages have been shown to highly infiltrate gliomas and largely contribute to the total tumor mass, so EphA3 was analyzed in relation to these sub-populations of tumor-infiltrating cells. Three markers of the monocyte/macrophage lineages were analyzed: CD68, CD163 and CD206 or mannose receptor. All three monocyte/macrophage markers co-localized with the EphA3 on a sub-population of cells surrounding the tumor vasculature.

Having established that EphA2 and EphA3 are promising molecular targets on GBM tumor cells, tumor neovasculature (EphA2), tumor-initiating and tumor-infiltrating cells of monocytic origin, efforts were focused on simultaneous targeting of these receptors. EphA3 and EphA2 receptors are both recognized by eA5. Eph receptors are activated by ligand binding and followed by receptor internalization. A recombinant dimeric form of eA5 was produces in fusion with the Fc region of human IgG1 (eA5-Fc). The chimera was active in inducing EphA2 receptor degradation 4 h after treatment on U-251 MG cells. The dimeric ligand induced massive EphA2 degradation starting at 4 h, and the protein level did not recover within the 48 h in U-251 MG cells. EphA3 protein level was reduced at 4 and 8 h post-treatment, increased at 24 h and was completely restored at 48 h when compared to non-treated (NT) cells control.

A dimeric eA5-PE38QQR cytotoxin was produced both as a recombinant non-glycosylated single chain chimeric protein termed eA5-PE-R and a chemically conjugated glycosylated form termed eA5-PE-C. The conjugated cytotoxin derived from cA5-Fc chemically linked to PE38QQR produced multiple forms of the conjugate, but the majority resulted in a 1:1 and 1:2 stoichiometric ratio between ligand and toxin.

The two cytotoxins were tested on human brain microvascular endothelial cells (HBMEC) and U-251 MG tumor cells using MTS/PMS cells viability assay. As expected, there was no killing effect on normal HBMEC cells after treatment with both recombinant and conjugated cytotoxin as well as the combination of eA5-Fc and PE38QQR. Conversely, we observed a potent effect of eA5-PE-C on U-251 MG cells. Assuming a 1:1 stoichiometric linkage between eA5-Fc and PE38QQR, the $IC_{50}$ of the conjugate was in the range of 10-11 M.

The recombinant form of the cytotoxin displayed lower activity than the conjugated one at higher concentrations while the mixture of eA5-Fc and PE38QQR did not produce any effect. EA5-PE-R cytotoxin formed protein aggregates, most likely due to the absence of the glycosylation on the dimeric eA5, similar to what is seen before on non-glycosylated eA1 (Ferluga et al., J Biol Chem June 21; 288(25): 18448-57). EA5-PE-R cytotoxin was additionally purified by size exclusion chromatography. One fraction (C10-C15) showed the expected MW of a dimeric recombinant cytotoxin (~150 kDa) and was indeed the only active fraction when tested by MTS/PMS viability assay on U-251 MG cells.

The effect of eA5-PE-C conjugated cytotoxin was also analyzed on several GBM cell lines. The cytotoxin was tested on U-251 MG, U-373 MG and G48a GBM cells, all three cell lines having high levels of both EphA2 and A3 receptors. As expected, the cytotoxin was very active in killing GBM cells overexpressing both EphA receptors. To confirm the specificity of the cytotoxin in targeting EphA2 and EphA3, the three GBM cell lines were pre-treated with either eA5-Fc or eA1-Fc at a concentration of 10 µg/mL for 1 hour. In the first case, the treatment with eA5-Fc should block both receptors limiting significantly the ability of cytotoxin to enter tumor cells. In the second case, eA1-Fc should bind only EphA2, so EphA3 should remain available to the cytotoxin. As expected, the cytotoxin was less active on the three cell lines tested when pre-treated with eA1-Fc, and lost most of its activity when cells were pre-treated with eA5-Fc.

The effect of eA5-PE-C was evaluated on three additional GBM cell lines, T98G and the two primary BTCOE4536 and BTCOE4795. These cells showed lower levels of one or both receptors by western blot analysis. The cell viability assay was performed at 48 and 72 h after cytotoxin administration. As expected, the effect of the cytotoxin was lower on these cells when compared to the cells having higher levels of both receptors, however, the cytotoxic effect of eA5-PE-C was still very potent when evaluated 72 h post-treatment.

EphA3 was found to be overexpressed in the majority of GBM specimens and present on tumor cells, in the invading ring of the tumor in particular, but not in normal brain. Additionally, EphA3 has been related to GBM tumor-initiating cells, as recently documented (Day et al., Cancer Cell February 11; 23(2):238-248 (2013)). However, herein is demonstrated that the EphA3 can be found also on tumor-infiltrating cells of monocytic origin, microglia/macrophage cells. These cells have been implicated in GBM progression (Li et al., Neuro Oncol August; 14(8):958-978). The distribution of EphA3 and EphA2, a receptor previously found in GBM (Wykosky et al., Mol Cancer Res October; 3(10):541-551 (2005)), differs to a large extent. Therefore, it is advantageous to target these receptors together in order to target multiple compartments of the tumor. EA5 can fulfill this role. An cA5-based chimeric cytotoxin, linking the eA5-Fc dimeric ligand to a truncated form of PE. The cytotoxin was specific in targeting GBM tumor cells expressing one or both receptors and triggering potent tumor cell killing.

GSCs are a small population of slow-dividing and self-renewing glioma cells characterized by an increase resistance to chemotherapy and radiotherapy (Ahmed et al., Expert Rev Neurother May; 13(5):545-555 (2013); Rycaj et al., Int J Radiat Biol, epub Mar. 7, 2014). It was found that the Eph receptor A3 is up-regulated in tumorspheres of G48a GBM cells. Not only was Eph receptor A3 protein level increased in tumorspheres, but we also observed a high degree of co-localization with the cancer stem cell marker Nestin. These data together suggested a role of EphA3 on tumor-initiating cells.

EphA3 receptor is overexpressed in approximately 60-70% of GBMs and in 20-30% of the lower-grade. No EphA3 was detected on the contralateral side of the diseased brain, and, most importantly, no co-localization was detected with adult neurons. EphA3 was also overexpressed in 55% of the established GBM cell lines tested, but not in glial cells.

The tumor microenvironment is a complex mixture of cells that together surround and support tumor cells (e.g., tumor vessels, cancer-associated fibroblasts, tumor-associated macrophages, tumor infiltrating lymphocytes, extracellular matrix, etc.), which can influence tumor progression and also therapeutic response/resistance of the treated lesion (Junttila et al., Nature September 19; 501(7467):346-354 (2013)).

The data reported herein provide strong evidence that EphA3 is present on tumor cells, tumor-initiating cells and tumor-infiltrating cells, while EphA2 is overexpressed on tumor cells and on tumor vasculature. The two receptors together are, therefore, overexpressed in the main subpopulations forming and supporting the tumor. EphA receptor A2 and A3, as well as EphB2, share the property of being activated upon binding with the same Ephrin ligand that can specifically and potently induce receptor internalization and down-regulation. This feature was used to design a novel eA5-based cytotoxin to target GBM cells overexpressing one or both receptors. The chimeric cytotoxin was generated by linking eA5 to PE38QQR. The ligand was produced in fusion with the Fc region of human IgG1 to allow eA5 dimerization, as this form is more active in inducing receptor internalization. EA5-Fc was tested on GBM cells actively inducing both EphA2 and EphA3 receptor down-regulation. EphA3 protein level reduced at 4 and 8 hours after treatment but recovered almost completely already at 24 hours, suggesting a faster turnover on cell membrane possibly explained by higher cytoplasmic protein levels. In the prospect of local delivery of an eA5-based therapeutic, a faster recovery of EphA3 may ensure that at least one targetable receptor is present back within hours of treatment.

Materials and Methods.

GBM cell lines U-251 MG, U-373 MG and T98G were obtained from the American Type Culture Collection (ATCC, Manassas, Va.) and grown in the ATCC recommended media. G48a cells were isolated in our laboratory from a human primary high-grade astrocytoma (50) and grown in RPMI medium with 10% (v/v) FBS and glucose adjusted to 4 g/L. All human samples were handled according to Wake Forest IRB protocol #8427. Human tumors specimens were obtained from the operating room and processed within 20 minutes of resection. Tumors were minced into small pieces and digested with Collagenase II, Collagenase IV and DNAse (Sigma) for 30 minutes at 370 C. The cell suspension was layered over a ficoll gradient and centrifuged at 300×g for 35 minutes. The interface was washed twice with PBS and the cells were cultured in RPMI-1640 containing 10% FBS and 4 g/L glucose. U-251 MG cells have been authenticated by Idexx Radil (Columbia, Mo.).

For flow cytometry analysis, 5×105 cells were harvested using Versene solution (Life technologies) and resuspended in 100 µL ice-cold PBS/0.1% bovine serum albumin (BSA); 2 µg of anti-EphA3 or anti-IgG antibody was added to each sample for 1 h. Cells were washed twice with 1 mL PBS/0.1% BSA and resuspended in 100 µL PBS/0.1% BSA. Secondary anti-rabbit antibody (1:50, AlexaFluor, Lifetech) was added to cells and incubated 1 h in the dark. Cells were washed twice with PBS/0.1% BSA, resuspended in 500 µL to a final concentration of 1×106 cells/mL, and subjected to analysis of at least 20,000 events per sample by FACS Calibur flow cytometer.

EphA2 and EphA3 down-regulation assay was performed as previously described for EphA2 (37). U-251 MG cells were treated with 1 µg/mL of recombinant eA5-Fc. Treated cells were incubated for 4 h before checking EphA2 and EphA3 degradation.

EA5 gene was synthesized (GenScript, Piscataway, N.J.) based on the GeneBank database (NCBI) sequence AAH75054.1. The gene was amplified by PCR using the forward primer BeA5Fc-F, 5'-TAAGGATCCCAGGAC- CCG-3' (SEQ ID NO:26) and the reverse primer: BeASFc-R, 5'-GTACAATTGCGGTGTCATCT-3' (SEQ ID NO:27) and cloned into BamHI-EcoRI sites in the modified Baculovirus transfer vector pAcGP67-B (BD Biosciences) (37, 49) and sequenced (Genewiz, Research Triangle Park, N.C.). Recombinant eA5 (aa. 21-191) was produced in the dimeric form (C-terminal Fc tag) in the Baculovirus expression system (BD Biosciences, San Diego, Calif.). Sf9 insect cells were co-transfected and protein collected as previously described (37, 49). Dimeric eA5 was purified by Protein G affinity chromatography (HiTrap Protein G HP, GE Healthcare) as recommended by the supplier. PE38QQR was produced and purify in house as previously described (38).

A 6×His tagged eA5 (21-191) was cloned upstream PE38QQR sequence in the pWD-MCS expression vector (38) with the following primers: eA5PE-F, 5'-AAACATAT-GCACCATCACCATCACCATCAGGACCCG-3' (SEQ ID NO:28) and eA5PE-R: 5'-TITAAGCCTGTCCTGAGC-CTCCTCGGTGTCATCTG-3'. (SEQ ID NO:29)

The dimeric recombinant eA5-PE-C cytotoxin was produced by adding the Fc tag sequence in frame in between eA5 and PE38QQR in the pWD-MCS expression vector with the following primers: Fc-F, 5'-TACTAAGCTTT-GACATGCCCACCGTGC-3' (SEQ ID NO:30) and Fc-R, 5'-ATCGAAGCTTGTTTACCCGGAGACAG-3' (SEQ ID NO:31). Recombinant eA5-PE-C was refolded and purified by ion exchange chromatography first and size exclusion after as previously described (38). Recombinant proteins purity was evaluated on Coommassie stained SDS-PAGE. Purified filtered proteins were stored in PBS at −80° C.

Protein chemical conjugation was achieved following the previously reported protocol (30) combining eA5-Fc to PE38QQR in a 1:3 molar ratio. The conjugated cytotoxin was additionally purified by size exclusion chromatography to remove any unconjugated protein and purity was evaluated by SDS-PAGE. Cell viability assays were performed to check cytotoxin activity using the CellTiter 96® AQueous Non-Radioactive Cell Proliferation Assay (MTS) following the instructions of the manufacturer (Promega). Cytotoxins were diluted to the appropriate concentrations in 1% PBS/BSA. One thousand cells/well were seeded in the 96 wellplate for U-251 MG and U-373 MG cells; 2.5×10³ cells/well for HBMEC, G48a, T980, BTCOE4536 and BTCOE4795 cells. Each cytotoxin concentration was tested in quadruplicate and cell viability was calculated as percentage of untreated control cells.

Cell lysates were prepared by lysing cells in RIPA buffer with proteases and phosphatases inhibitors (Sigma), and separated by 10% SDS-PAGE. Western blotting was performed as previously described (14). Primary antibodies from Santa Cruz Biotechnology (Santa Cruz, Calif.) included: rabbit polyclonal EphA3 (C-19) (1:1000), rabbit polyclonal EphA3 (L-18) (1:1000), mouse monoclonal ephrin-A5 (RR-7), rabbit polyclonal eA1 (V-18)(1:1000). Other antibodies used were: EphA2 mouse monoclonal (clone D7) (1:1000, EMD Millopore Corporation, Billerica, Mass. and Sigma-Aldrich, Saint Louis, Mo.) and β-actin (1:50000, Sigma). Anti-rabbit and anti-mouse secondary antibodies (Sigma) were used 1:5000. Films were scanned at a resolution of 400 dpi using a HP ScanJet3979 and Adobe Photoshop 5.0 Software.

For immunofluorescent staining, cells were grown overnight on sterile glass slides in the appropriate media. Slides were washed twice in phosphate-buffered saline (PBS) and fixed for 2 min in acetone at −20° C., washed twice again in PBS and blocked for 1 h in 5% PBS/bovine serum albumin (BSA) at room temperature. EphA3 clone C19 (1:250, Santa Cruz), EphA2 clone D7 (1:100, Millipore), NeuN clone A60 (1:300, Millipore), GFAP (1:250, Santa Cruz), CD31 (1:300, Pierce), CD68 clone SPM281 (1:100, Novus Biologicals), CD163 clone 5C6FAT (1:300, Novus Biologicals) and CD206 clone 15-2 (1:100, Santa Cruz) primary antibodies were diluted in 1% PBS/BSA and incubated overnight at 4° C. Slides were then washed twice in PBS, 5 min each, and incubated with secondary antibodies (1:200, AlexaFluor, Lifetech) and Nuclear Counterstain (DAPI, 1:1000) in 1% PBS/BSA for 1 h at room temperature. Slides were washed two times for 5 min each in PBS and mounted with fluoroguard. Photomicrographs were taken using ImagePro Plus software with minimal adjustments of brightness and contrast.

REFERENCES

1. Hottinger A F, Stupp R, Homicsko K. Standards of care and novel approaches in the management of glioblastoma multiforme. Chin J Cancer January; 33(1):32-9.
2. Ramirez Y P, Weatherbee J L, Wheelhouse R T, Ross A H. Glioblastoma multiforme therapy and mechanisms of resistance. Pharmaceuticals (Basel); 6(12):1475-506.
3. Nieder C, Adam M, Grosu A L. Combined modality treatment of glioblastoma multiforme: the role of temozolomide. Rev Recent Clin Trials 2006 January; 1(1):43-51.
4. Yang L J, Zhou C F, Lin Z X. Temozolomide and radiotherapy for newly diagnosed glioblastoma multiforme: a systematic review. Cancer Invest February; 32(2):31-6.
5. Jovcevska I, Kocevar N, Komel R. Glioma and glioblastoma—how much do we (not) know?Mol Clin Oncol November; 1(6):935-41.
6. Lefranc F, Rynkowski M, DeWitte O, Kiss R. Present and potential future adjuvant issues in high-grade astrocytic glioma treatment. Adv Tech Stand Neurosurg 2009; 34:3-35.
7. Schonberg D L, Lubelski D, Miller T E, Rich J N. Brain tumor stem cells: Molecular characteristics and their impact on therapy. Mol Aspects Med July 4.
8. Agarwal S, Manchanda P, Vogelbaum M A, Ohlfest J R, Elmquist W F. Function of the blood-brain barrier and restriction of drug delivery to invasive glioma cells: findings in an orthotopic rat xenograft model of glioma. Drug Metab Dispos January; 41(1):33-9.
9. Debinski W, Tatter S B. Convection-enhanced delivery for the treatment of brain tumors. Expert Rev Neurother 2009 October; 9(10):1519-27.
10. Kunwar S, Chang S, Westphal M, et al. Phase H I randomized trial of CED of IL13-PE38QQR vs Gliadel wafers for recurrent glioblastoma. Neuro Oncol August; 12(8):871-81.
11. Cloughesy T F, Cavenee W K, Mischel P S. Glioblastoma: from molecular pathology to targeted treatment. Annu Rev Pathol; 9:1-25.
12. Wykosky J, Gibo D M, Stanton C, Debinski W. Interleukin-13 receptor alpha 2, EphA2, and Fos-related antigen 1 as molecular denominators of high-grade astrocytomas and specific targets for combinatorial therapy. Clin Cancer Res 2008 Jan. 1; 14(1):199-208.
13. Chow K K, Naik S, Kakarla S, et al. T cells redirected to EphA2 for the immunotherapy of glioblastoma. Mol Ther March; 21(3):629-37.
14. Wykosky J, Gibo D M, Stanton C, Debinski W. EphA2 as a novel molecular marker and target in glioblastoma multiforme. Mol Cancer Res 2005 October; 3(10):541-51.

15. Day B W, Stringer B W, Al-Ejeh F, et al. EphA3 maintains tumorigenicity and is a therapeutic target in glioblastoma multiforme. Cancer Cell February 11; 23(2): 238-48.
16. Verhaak R G, Hoadley K A, Purdom E, et al. Integrated genomic analysis identifies clinically relevant subtypes of glioblastoma characterized by abnormalities in PDGFRA, IDH1, EGFR, and NF1. Cancer Cell January 19; 17(1): 98-110.
17. Nikolov D B, Xu K, Himanen J P. Eph/ephrin recognition and the role of Eph/ephrin clusters in signaling initiation. Biochim Biophys Acta October; 1834(10): 2160-5.
18. Lisabeth E M, Falivelli G, Pasquale E B. Eph receptor signaling and ephrins. Cold Spring Harb Perspect Biol September; 5(9).
19. Park S. Brain-Region Specific Apoptosis Triggered by Eph/ephrin Signaling. Exp Neurobiol September; 22(3): 143-8.
20. Gao Q, Liu W, Cai J, et al. EphB2 promotes cervical cancer progression by inducing epithelial-mesenchymal transition. Hum Pathol February; 45(2):372-81.
21. Irizarry-Ramirez M, Willson C A, Cruz-Orengo L, et al. Upregulation of EphA3 receptor after spinal cord injury. J Neurotrauma 2005 August; 22(8):929-35.
22. Taddei M L, Parri M, Angelucci A, et al. EphA2 induces metastatic growth regulating amoeboid motility and clonogenic potential in prostate carcinoma cells. Mol Cancer Res February; 9(2):149-60.
23. Lu C Y, Yang Z X, Zhou L, et al. High levels of EphA3 expression are associated with high invasive capacity and poor overall survival in hepatocellular carcinoma. Oncol Rep November; 30(5):2179-86.
24. Wang S D, Rath P, Lal B, et al. EphB2 receptor controls proliferation/migration dichotomy of glioblastoma by interacting with focal adhesion kinase. Oncogene December 13; 31(50):5132-43.
25. Lu Z, Zhang Y, Li Z, et al. Overexpression of the B-type Eph and ephrin genes correlates with progression and pain in human pancreatic cancer. Oncol Lett June; 3(6):1207-12.
26. Weidle U H, Tiefenthaler G, Schiller C, Weiss E H, Georges G, Brinkmann U. Prospects of bacterial and plant protein-based immunotoxins for treatment of cancer. Cancer Genomics Proteomics January-February; 11(1):25-38.
27. Debinski W. Local treatment of brain tumors with targeted chimera cytotoxic proteins. Cancer Invest 2002; 20(5-6):801-9.
28. Baiz D, Hassan S, Choi Y A, et al. Combination of the PI3K inhibitor ZSTK474 with a PSMA-targeted immunotoxin accelerates apoptosis and regression of prostate cancer. Neoplasia October; 15(10):1172-83.
29. Li Y M, Hall W A. Targeted toxins in brain tumor therapy. Toxins (Basel) November; 2(11):2645-62.
30. Wykosky J, Gibo D M, Debinski W. A novel, potent, and specific ephrinA1-based cytotoxin against EphA2 receptor expressing tumor cells. Mol Cancer Ther 2007 December; 6(12 Pt 1):3208-18.
31. Himanen J P, Chumley M J, Lackmann M, et al. Repelling class discrimination: ephrin-A5 binds to and activates EphB2 receptor signaling. Nat Neurosci 2004 May; 7(5):501-9.
32. Himanen J P, Yermekbayeva L, Janes P W, et al. Architecture of Eph receptor clusters. Proc Natl Acad Sci USA June 15; 107(24):10860-5.
33. Li S C, Vu L T, Ho H W, et al. Cancer stem cells from a rare form of glioblastoma multiforme involving the neurogenic ventricular wall. Cancer Cell Int; 12(1):41.
34. Lyubimova N V, Toms M G, Fu R G, Bondarenko Y V. Biochemical markers of brain tumours. Klin Lab Diagn October(10):71-2, 40-2.
35. Graeber M B, Scheithauer B W, Kreutzberg G W. Microglia in brain tumors. Glia 2002 November; 40(2): 252-9.
36. Li W, Graeber M B. The molecular profile of microglia under the influence of glioma. Neuro Oncol August; 14(8):958-78.
37. Ferluga S, Hantgan R, Goldgur Y, Himanen J P, Nikolov D B, Debinski W. Biological and structural characterization of glycosylation on ephrin-A1, a preferred ligand for EphA2 receptor tyrosine kinase. J Biol Chem June 21; 288(25): 18448-57.
38. Debinski W, Pastan I. Monovalent immunotoxin containing truncated form of *Pseudomonas* exotoxin as potent antitumor agent. Cancer Res 1992 October 1; 52(19):5379-85.
39. Walker-Daniels J, Riese D J, 2nd, Kinch M S. c-Cbl-dependent EphA2 protein degradation is induced by ligand binding. Mol Cancer Res 2002 November; 1(1): 79-87.
40. Tandon M, Vemula S V, Mittal S K. Emerging strategies for EphA2 receptor targeting for cancer therapeutics. Expert Opin Ther Targets January; 15(1):31-51.
41. Boyd A W, Bartlett P F, Lackmann M. Therapeutic targeting of EPH receptors and their ligands. Nat Rev Drug Discov January; 13(1):39-62.
42. Nievergall E, Saunders T, Lackmann M. Targeting of EPH receptor tyrosine kinases for anticancer therapy. Crit Rev Oncog; 17(2):211-32.
43. Ahmed A U, Auffinger B, Lesniak M S. Understanding glioma stem cells: rationale, clinical relevance and therapeutic strategies. Expert Rev Neurother May; 13(5):545-55.
44. Rycaj K, Tang D G. Cancer stem cells and radioresistance. Int J Radiat Biol March 7.
45. Wykosky J, Palma E, Gibo D M, Ringler S, Turner C P, Debinski W. Soluble monomeric EphrinA1 is released from tumor cells and is a functional ligand for the EphA2 receptor. Oncogene 2008 December 11; 27(58):7260-73.
46. Junttila M R, de Sauvage F J. Influence of tumour micro-environment heterogeneity on therapeutic response. Nature September 19; 501(7467):346-54.
47. Ladeby R, Wirenfeldt M, Dalmau I, et al. Proliferating resident microglia express the stem cell antigen CD34 in response to acute neural injury. Olia 2005 Apr. 15; 50(2): 121-31.
48. Anam K, Davis T A. Comparative analysis of gene transcripts for cell signaling receptors in bone marrow-derived hematopoietic stem/progenitor cell and mesenchymal stromal cell populations. Stem Cell Res Ther, 4(5):112.
49. Lema Tome C M, Palma B, Ferluga S, et al. Structural and functional characterization of monomeric EphrinA1 binding site to EphA2 receptor. J Biol Chem April 20; 287(17):14012-22.
50. Debinski W, Gibo D M. Fos-related antigen 1 modulates malignant features of glioma cells. Mol Cancer Res 2005 April; 3(4):237-49.

Example 3

Targeting Four Receptors with One Compound

A fusion construct is provided to target four receptors with one compound. The binding properties of eA5 and IL-13 variants are exploited in the construction of an IgG scaffold-based single molecule, which will have an ability to bind IL-13Rα2, EPHA2, EPHA3 and EphB2 and to deliver a catalyst to targeted cells with ensuing potent and specific cell kill.

Generation of a Multi-Valent Cytotoxin (QUAD-CTX) Targeting all Principal Compartments of GBM Tumors.

A cytotoxin targeting concomitantly IL-13RA2, EPHA2, EPHA3 and EPHB2 receptors is produced. See FIG. 7. The cytotoxin is based on an IgG scaffold and eA5 and IL-13 mutant binding moieties. The cytotoxin is tested in in vitro and in vivo models of various compartments of GBM.

Phase I Clinical Trial with QUAD-CTX in Patients with Recurrent GBM.

A single-institution Phase I clinical trial is performed with QUAD-CTX using CED with real-time MRI monitoring of drug delivery and distribution. The trial is a dose-escalation with a primary objective to determine safety and tolerability of QUAD-CTX. The drug is given in at least two cycles of 48-hr continuous infusions.

Thus, provided is a molecularly targeted anti-GBM drug that: (i) does not require patients pre-screening before treatment, (ii) attacks the most important pathobiologically compartments of the tumor, and (iii) performs these functions in one molecular entity meaning that it will be suitable for monotherapy. It is expected that this all-out assault on GBM will translate into clear-cut, durable responses in patients.

Example 4

Generation and Testing of eA5 Mutants with Enhanced Ephrin Receptor Binding Affinity The G-H loop, a highly conserved among ephrinA (eA) ligands, has been confirmed to be the region that mediates eA binding to EphA2. Mutations of P113 to A, T115 to A and 0117 to A, as well as E122 to A and to some extent Q109 to A, of the eA1 G-H loop result in enhanced binding affinity of these eA1 mutants to EphA2. See Lema Tome et al., J Biol Chem 287:14012-14022 (2012). The analogous positions to P113, T115 and G117 in the G-H loop of eA1 (UniProtKB/Swiss-Prot Accession No. P20827.2), in the G-H loop of eA5 (UniProtKB/Swiss-Prot Accession No. P52803.1) are P123, S125 and G127, respectively.

The eA5 mutants P123A (P to A), S125A (S to A) and G127A (G to A) are generated by known methods, using a transformer site-directed mutagenesis kit (Clonetech, Mountain View, Calif.) and a plasmid that expresses eA5 and are produced using a baculovirus expression vector system from BD Biosciences.

Binding interactions of eA5 mutants is determined by surface Plasmon resonance. Functional activity of eA5 mutants are determined by EphA2 down regulation, ERK activation, AKT activation and cellular response assays. See Lema Tome et al., J Biol Chem 287:14012-14022 (2012).

The selected eA5 mutants generated are expected to have enhanced binding affinity for EphA2. The enhanced binding affinity of these eA5 mutants results in enhanced EphA2 down-regulation, AKT and ERK activation over wild-type eA5. Other eA5 mutants, with mutations at more than one, two or even three, of the amino acids substituted with A, that result in enhanced binding to EphA2 over wild-type, are made.

The eA5 mutants generated are also examined for their binding affinity to EphA3 and EphB2. The eA5 mutants (eA5M) exhibiting enhanced binding affinity for EphA2, as well as EphA3 and/or EphB2, over wild-type eA5 are used in preparing improved QUAD-CTX therapeutics, as described in Example 3. See, FIG. 7.

Example 5

Bivalent Construct Activity

The bivalent construct eA5-Fc-IL-13.E13K was tested for activity. As shown in FIG. 8, the construct was shown to down-regulate the EphA2 receptor (from eA5).

Further, the construct was able to neutralize the action of IL-13 based cytotoxin (from IL-13.E13K), as shown in FIG. 9. Cell receptors were blocked with equimolar (125 nM) concentration of IL.E13K (squares) and eA5-Fc-IL-13.E13K for one hour. After one hour, IL-13.E13K-P38QQR toxin was added in a concentration range of 100 nM-0.1 nM. Circles represent only toxin without any blocker protein. eA5-Fc alone (w/o IL-13-E.13K) was not capable of such neutralization.

The foregoing is illustrative of the present invention, and is not to be construed as limiting thereof. The invention is defined by the following claims, with equivalents of the claims to be included therein.

That which is claimed is:

1. A construct comprising, in combination: a ligand that binds to all three of EphA2, EphA3 and EphB2; a ligand that binds to IL-13Rα2; and at least one effector molecule, wherein said construct is a fusion protein and/or a covalent conjugate, wherein said construct has a first end and a second end, said first end comprising said ligand that binds to all three of EphA2, EphA3 and EphB2; and said second end comprising said ligand that binds to IL-13Rα2, and wherein said construct comprises a linker between said first end and said second end.

2. The construct of claim 1, wherein said construct is a covalent conjugate of two or more fusion proteins.

3. The construct of claim 1, wherein said ligand that binds to all three of EphA2, EphA3 and EphB2 is a monomer or dimer of: eA5; a mutant of eA5; or an EphA2, EphA3 and EphB2 binding fragment thereof.

4. The construct of claim 3, wherein said eA5, mutant of eA5, or EphA2, EphA3 and EphB2 binding fragment thereof is glycosylated.

5. The construct of claim 1, wherein said ligand that binds to IL-13Rα2 is:

IL-13;

a mutant of IL-13; or an IL-13Rα2 binding fragment thereof.

6. The construct of claim 1, wherein said linker between said first end and said second end is a protein linker.

7. The construct of claim 6, wherein said protein linker comprises an ADCC and/or CDC activating domain.

8. The construct of claim 6, wherein said protein linker comprises an Fc fragment of human IgG$_1$.

9. The construct of claim 1, wherein said ligand that binds to all three of EphA2, EphA3 and EphB2 is a monomer or dimer of: a mutant of eA5.

10. The construct of claim 9, wherein the mutant of eA5 comprises a P123A, S125A and/or G127A mutation.

* * * * *

UNITED STATES PATENT AND TRADEMARK OFFICE
CERTIFICATE OF CORRECTION

PATENT NO. : 9,975,942 B2
APPLICATION NO. : 15/035560
DATED : May 22, 2018
INVENTOR(S) : Debinski et al.

Page 1 of 2

It is certified that error appears in the above-identified patent and that said Letters Patent is hereby corrected as shown below:

On the Title Page

Item (56) References Cited, Other Publications, 1st Day B et al. cite:
Please correct "238-428. Day B et al." to read -- 238-428. --

Item (56) References Cited, Other Publications, Day B et al. cite of Jul. 2005:
Please correct "Three distinct molecular surfaces" to read -- Day B et al., Three distinct molecular surfaces --

Item (56) References Cited, Other Publications, Day B et al. cite of Jul. 2005:
Please correct "270(8)" to read -- 270(28) --

In the Specification

Column 2, Line 15:
Please correct "EpbA2" to read -- EphA2 --

Column 4, Line 18:
Please correct "0204" to read -- G204 --

Column 4, Line 58:
Please correct "cA1-Fc" to read -- eA1-Fc --

Column 8, Line 63:
Please correct "WHO grade II" to read -- WHO grade III --

Column 16, Line 6:
Please correct "E-D-C-O-F" to read -- E-D-C-G-F --

Signed and Sealed this
Fourth Day of September, 2018

Andrei Iancu
*Director of the United States Patent and Trademark Office*

CERTIFICATE OF CORRECTION (continued)
U.S. Pat. No. 9,975,942 B2

Column 29, Line 41:
Please correct "cA5" to read -- eA5 --

Column 31, Line 1:
Please correct "BeASFc-" to read -- BeA5Fc- --

Column 31, Lines 18-19:
Please correct "5'-TITAAGCCTGTCCTGAGC-CTCCTCGGTGTCATCTG-3'" to read
-- 5'-TTTAAGCTTGTCCTGAGCCTCCGGTGTCATCTG-3' --

Column 31, Line 43:
Please correct "T980" to read -- T98G --

Column 35, Line 38:
Please correct "0117" to read -- G117 --